(12) United States Patent
Manzo

(10) Patent No.: US 8,123,102 B2
(45) Date of Patent: Feb. 28, 2012

(54) ANASTOMOSIS INSTRUMENT AND METHOD FOR PERFORMING SAME

(75) Inventor: Scott E. Manzo, Shelton, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 13/227,981

(22) Filed: Sep. 8, 2011

(65) Prior Publication Data

US 2012/0004678 A1 Jan. 5, 2012

Related U.S. Application Data

(63) Continuation of application No. 12/203,964, filed on Sep. 4, 2008, now Pat. No. 8,025,198, which is a continuation of application No. 11/300,101, filed on Dec. 13, 2005, now Pat. No. 7,422,137, which is a continuation of application No. 10/182,215, filed on Jul. 25, 2002, now Pat. No. 7,223,273.

(60) Provisional application No. 60/176,697, filed on Jan. 18, 2000.

(51) Int. Cl.
*A61B 17/068* (2006.01)

(52) U.S. Cl. ............. 227/176.1; 227/19; 227/175.2; 606/143; 606/153; 606/219

(58) Field of Classification Search ........... 227/19, 227/179.1, 176.1, 175.2, 175.3, 175.1; 606/153, 606/219, 142, 143
See application file for complete search history.

(56) References Cited

U.S. PATENT DOCUMENTS

| | | | |
|---|---|---|---|
| 3,232,089 A | 2/1966 | Samuels et al. | |
| 3,366,301 A | 1/1968 | Mallina | |
| 3,519,187 A | 7/1970 | Kapitanov et al. | |
| 3,771,526 A | 11/1973 | Rudie | |
| 4,166,466 A | 9/1979 | Jarvik | |
| 4,350,160 A | 9/1982 | Kolesov et al. | |
| 4,368,736 A | 1/1983 | Kaster | |
| 4,467,804 A | 8/1984 | Hardy et al. | |
| 4,476,863 A | 10/1984 | Kanshin et al. | |
| D276,650 S | 12/1984 | Green et al. | |
| 4,552,148 A | 11/1985 | Hardy et al. | |
| 4,708,141 A | 11/1987 | Inoue et al. | |
| 4,752,024 A | 6/1988 | Green et al. | |
| 4,766,898 A | 8/1988 | Hardy et al. | |
| 4,872,874 A | 10/1989 | Taheri | |

(Continued)

FOREIGN PATENT DOCUMENTS

EP 384647 2/1990

(Continued)

OTHER PUBLICATIONS

International Search Report—EP97112634—Dec. 17, 1997.
International Search Report—EP98110977—Sep. 25, 1998.

(Continued)

*Primary Examiner* — Scott A. Smith

(57) ABSTRACT

A surgical instrument for creating an anastomosis includes a housing, a handle extending from the housing and a fastener support member extending distally from the housing. The fastener support member is configured and dimensioned to releasably support a plurality of surgical fasteners. The instrument further includes a tissue retaining mechanism which is selectively movable from a first position relative to the fastener support member to a second position in closer proximity with the fastener support member such that tissue disposed adjacent to the fastener support member is retained thereagainst. Upon actuation of the handle, a fastener firing mechanism simultaneously deforms the plurality of surgical fasteners to complete the anastomosis.

6 Claims, 20 Drawing Sheets

U.S. PATENT DOCUMENTS

| | | | |
|---|---|---|---|
| 4,893,622 A | 1/1990 | Green et al. |
| 4,899,744 A | 2/1990 | Fujitsuka et al. |
| 4,907,591 A | 3/1990 | Vasconcellos et al. |
| 4,917,114 A | 4/1990 | Green et al. |
| 4,930,674 A | 6/1990 | Barak |
| 4,931,057 A | 6/1990 | Cummings et al. |
| 4,957,499 A | 9/1990 | Lipatov et al. |
| 4,979,954 A | 12/1990 | Gwathmey et al. |
| 5,025,779 A | 6/1991 | Bugge |
| 5,188,638 A | 2/1993 | Tzakis |
| 5,211,649 A | 5/1993 | Kohler et al. |
| 5,222,963 A | 6/1993 | Brinkerhoff et al. |
| 5,234,447 A | 8/1993 | Kaster et al. |
| 5,250,058 A | 10/1993 | Miller et al. |
| 5,282,810 A | 2/1994 | Allen et al. |
| 5,314,436 A | 5/1994 | Wilk |
| 5,346,501 A | 9/1994 | Regula et al. |
| 5,354,304 A | 10/1994 | Allen et al. |
| 5,366,458 A | 11/1994 | Korthoff et al. |
| 5,366,462 A | 11/1994 | Kaster et al. |
| 5,403,333 A | 4/1995 | Kaster et al. |
| 5,403,338 A | 4/1995 | Milo |
| 5,425,738 A | 6/1995 | Gustafson et al. |
| 5,431,668 A | 7/1995 | Burbank, III et al. |
| 5,437,684 A | 8/1995 | Calabrese et al. |
| 5,443,198 A | 8/1995 | Viola et al. |
| 5,452,733 A | 9/1995 | Sterman et al. |
| 5,474,732 A | 12/1995 | Korthoff et al. |
| 5,485,947 A | 1/1996 | Olson et al. |
| 5,486,187 A | 1/1996 | Schenck |
| 5,503,635 A | 4/1996 | Sauer et al. |
| 5,649,937 A | 7/1997 | Bito et al. |
| 5,658,300 A | 8/1997 | Bito et al. |
| 5,669,918 A | 9/1997 | Balazs et al. |
| 5,695,504 A | 12/1997 | Gifford, III et al. |
| 5,697,943 A | 12/1997 | Sauer et al. |
| 5,702,412 A | 12/1997 | Popov et al. |
| 5,707,380 A | 1/1998 | Hinchliffe et al. |
| 5,709,335 A | 1/1998 | Heck |
| 5,725,537 A | 3/1998 | Green et al. |
| 5,732,872 A | 3/1998 | Bolduc et al. |
| 5,779,718 A | 7/1998 | Green et al. |
| 5,797,931 A | 8/1998 | Bito et al. |
| 5,797,934 A | 8/1998 | Rygaard |
| 5,817,113 A | 10/1998 | Gifford, III et al. |
| 5,823,956 A | 10/1998 | Roth et al. |
| 5,827,316 A | 10/1998 | Young et al. |
| 5,833,698 A | 11/1998 | Hinchliffe et al. |
| 5,839,639 A | 11/1998 | Sauer et al. |
| 5,855,614 A | 1/1999 | Stevens et al. |
| 5,860,581 A | 1/1999 | Robertson et al. |
| 5,881,943 A | 3/1999 | Heck et al. |
| 5,891,160 A | 4/1999 | Williamson, IV et al. |
| 5,904,697 A | 5/1999 | Gifford, III et al. |
| 5,906,625 A | 5/1999 | Bito et al. |
| 5,916,226 A | 6/1999 | Tozzi |
| 5,944,730 A | 8/1999 | Nobles et al. |
| 5,947,363 A | 9/1999 | Bolduc et al. |
| 5,951,576 A | 9/1999 | Wakabayashi |
| 5,957,363 A | 9/1999 | Heck |
| 5,957,879 A | 9/1999 | Roberts et al. |
| 5,961,481 A | 10/1999 | Sterman et al. |
| 5,964,782 A | 10/1999 | Lafontaine et al. |
| 5,971,973 A | 10/1999 | Peters |
| 5,972,030 A | 10/1999 | Garrison et al. |
| 5,976,159 A | 11/1999 | Bolduc et al. |
| 5,993,468 A | 11/1999 | Rygaard |
| 6,015,416 A | 1/2000 | Stefanchik et al. |
| 6,024,748 A | 2/2000 | Manzo |
| 6,030,395 A | 2/2000 | Nash et al. |
| 6,036,705 A | 3/2000 | Nash et al. |
| 6,056,762 A | 5/2000 | Nash et al. |
| 6,066,144 A | 5/2000 | Wolf et al. |
| 6,080,173 A | 6/2000 | Williamson, IV et al. |
| 6,083,234 A | 7/2000 | Nicholas et al. |
| 6,110,187 A | 8/2000 | Donlon |
| 6,171,319 B1 | 1/2001 | Nobles et al. |
| 6,171,321 B1 | 1/2001 | Gifford, III et al. |
| 6,176,413 B1 | 1/2001 | Heck et al. |
| 6,176,864 B1 | 1/2001 | Chapman |
| 6,183,486 B1 | 2/2001 | Snow et al. |
| 6,187,019 B1 | 2/2001 | Stefanchik et al. |
| 6,187,020 B1 | 2/2001 | Zegdi et al. |
| 6,187,022 B1 | 2/2001 | Alexander, Jr. et al. |
| 6,190,397 B1 | 2/2001 | Spence et al. |
| 6,190,590 B1 | 2/2001 | Randall et al. |
| 6,193,734 B1 | 2/2001 | Bolduc et al. |
| 6,197,042 B1 | 3/2001 | Ginn et al. |
| 6,206,913 B1 | 3/2001 | Yencho et al. |
| 6,231,506 B1 | 5/2001 | Hu et al. |
| 6,234,995 B1 | 5/2001 | Peacock, III |
| 6,241,741 B1 | 6/2001 | Duhaylongsod et al. |
| 6,241,742 B1 | 6/2001 | Spence et al. |
| 6,241,743 B1 | 6/2001 | Levin et al. |
| 6,248,117 B1 | 6/2001 | Blatter |
| 6,253,984 B1 | 7/2001 | Heck et al. |
| 6,254,615 B1 | 7/2001 | Bolduc et al. |
| 6,254,617 B1 | 7/2001 | Spence et al. |
| 6,280,460 B1 | 8/2001 | Bolduc et al. |
| 6,332,468 B1 | 12/2001 | Benetti |
| 6,338,712 B2 | 1/2002 | Spence et al. |
| 6,346,074 B1 | 2/2002 | Roth |
| 6,350,252 B2 | 2/2002 | Ray et al. |
| 6,361,543 B1 | 3/2002 | Chin et al. |
| 6,371,965 B2 | 4/2002 | Gifford, III et al. |
| 6,387,105 B1 | 5/2002 | Gifford, III et al. |
| 6,391,039 B1 | 5/2002 | Nicholas et al. |
| 6,401,721 B1 | 6/2002 | Maginot |
| 6,440,146 B2 | 8/2002 | Nicholas et al. |
| 6,443,965 B1 | 9/2002 | Gifford, III et al. |
| 6,450,390 B2 | 9/2002 | Heck et al. |
| 6,451,034 B1 | 9/2002 | Gifford, III et al. |
| 6,461,365 B2 | 10/2002 | Bolduc et al. |
| 6,471,713 B1 | 10/2002 | Vargas et al. |
| 6,503,259 B2 | 1/2003 | Huxel et al. |
| 6,562,037 B2 | 5/2003 | Paton et al. |
| 6,726,697 B2 | 4/2004 | Nicholas et al. |
| 6,769,594 B2 | 8/2004 | Orban, III |
| 6,962,596 B2 | 11/2005 | Bolduc et al. |
| 7,029,482 B1 | 4/2006 | Vargas et al. |
| 7,041,110 B2 | 5/2006 | Yencho et al. |
| 7,223,273 B2 | 5/2007 | Manzo |
| 7,351,247 B2 | 4/2008 | Kupiecki et al. |
| 7,422,137 B2 | 9/2008 | Manzo |
| 8,025,198 B2 * | 9/2011 | Manzo ........................ 227/176.1 |
| 2003/0171775 A1 | 9/2003 | Belson |
| 2003/0181930 A1 | 9/2003 | Milliman et al. |
| 2003/0208213 A1 | 11/2003 | Manzo |
| 2004/0078047 A1 | 4/2004 | Nicholas et al. |
| 2004/0082963 A1 | 4/2004 | Gannoe et al. |
| 2004/0092971 A1 | 5/2004 | Sniffin et al. |
| 2004/0092974 A1 | 5/2004 | Gannoe et al. |
| 2004/0199182 A1 | 10/2004 | Milliman et al. |
| 2005/0087580 A1 | 4/2005 | Orban |

FOREIGN PATENT DOCUMENTS

| | | |
|---|---|---|
| EP | 594004 | 4/1994 |
| EP | 643946 | 3/1995 |
| EP | 656191 | 6/1995 |
| EP | 820725 | 7/1997 |
| EP | 820724 | 1/1998 |
| EP | 885595 | 12/1998 |
| EP | 1088519 | 4/2001 |
| FR | 1518083 | 2/1968 |
| FR | 2777446 | 10/1999 |
| GB | 935490 | 8/1963 |
| WO | WO88/01486 | 3/1988 |
| WO | WO95/15715 | 6/1995 |
| WO | WO95/17127 | 6/1995 |
| WO | WO95/35065 | 12/1995 |
| WO | WO97/40754 | 11/1997 |
| WO | WO99/11178 | 3/1999 |
| WO | WO00/69343 | 11/2000 |
| WO | WO01/52748 | 7/2001 |
| WO | WO02/32323 | 4/2002 |
| WO | WO02/058568 | 8/2002 |
| WO | WO03/101314 | 12/2003 |

OTHER PUBLICATIONS

International Search Report—EP99118064—Nov. 1, 2000.
International Search Report—EP0120262—Dec. 20, 2000.
International Search Report—PCT/US01/02043—Nov. 7, 2001.
International Search Report—PCT/US02/00345—May 24, 2002.
International Search Report—PCT/US03/18295—Oct. 28, 2003.
Information Booklet for: LIGACLIP, Ligating Clips, Appliers & Removers for security in Ligation, Ethicon, Inc., 1982.
Information Booklet for: Deep Surgery Advantage—Dramatic New Access Plus Automatic-Feed in Vessel Ligation, Hemoclip® automatic ligating clip system, Edward Weck & Company, Inc. Sep. 1996.
Information Booklet for: Auto Suture® Premium Surgliclip™ Titanium disposable automatic clip appliers, United States Surgical Corporation, 1981.

* cited by examiner

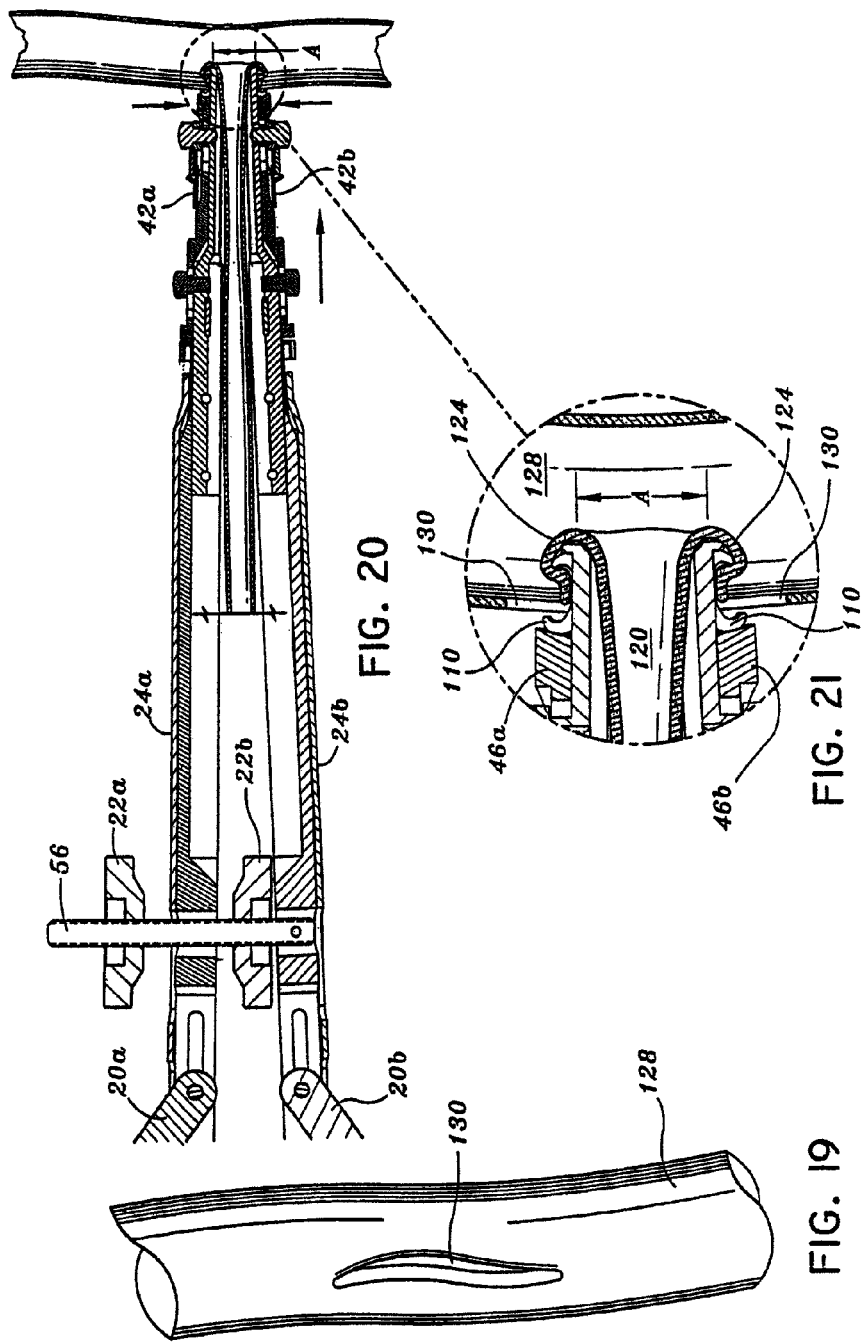

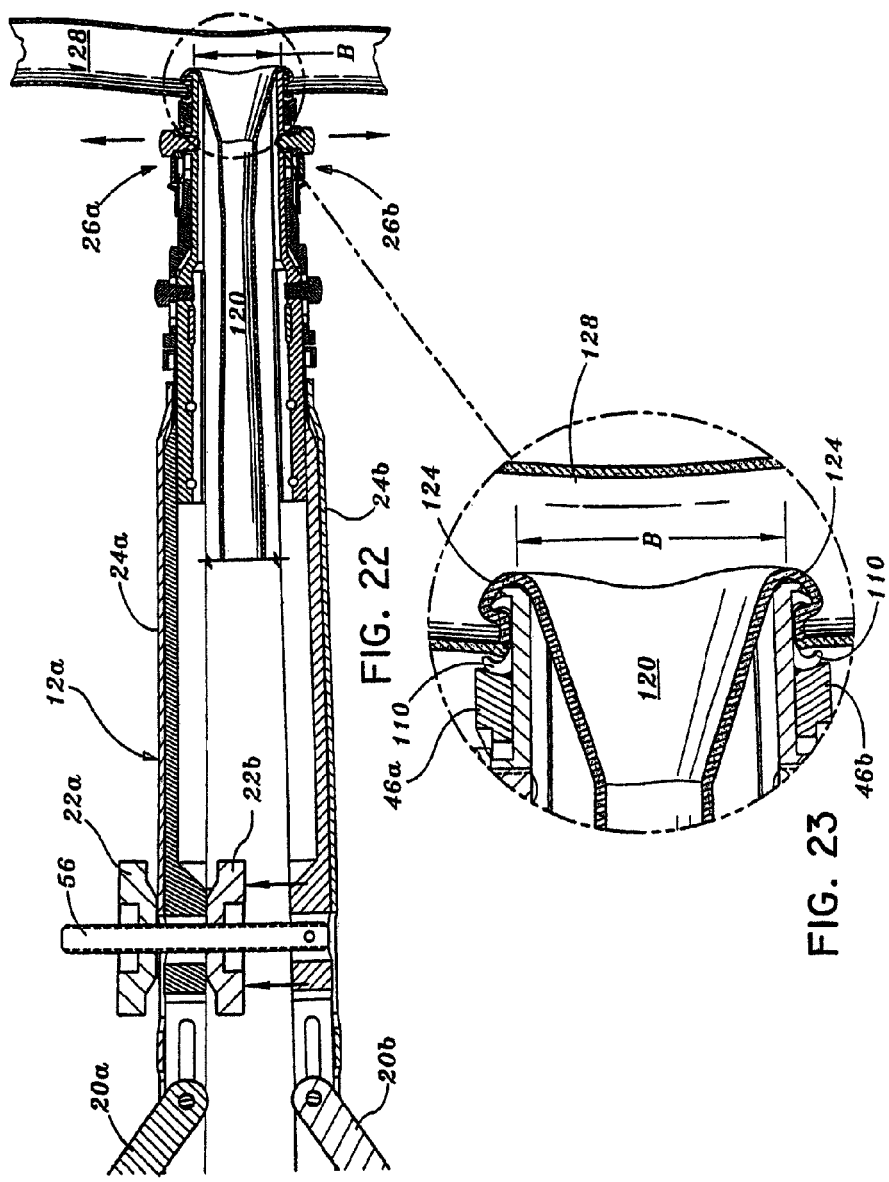

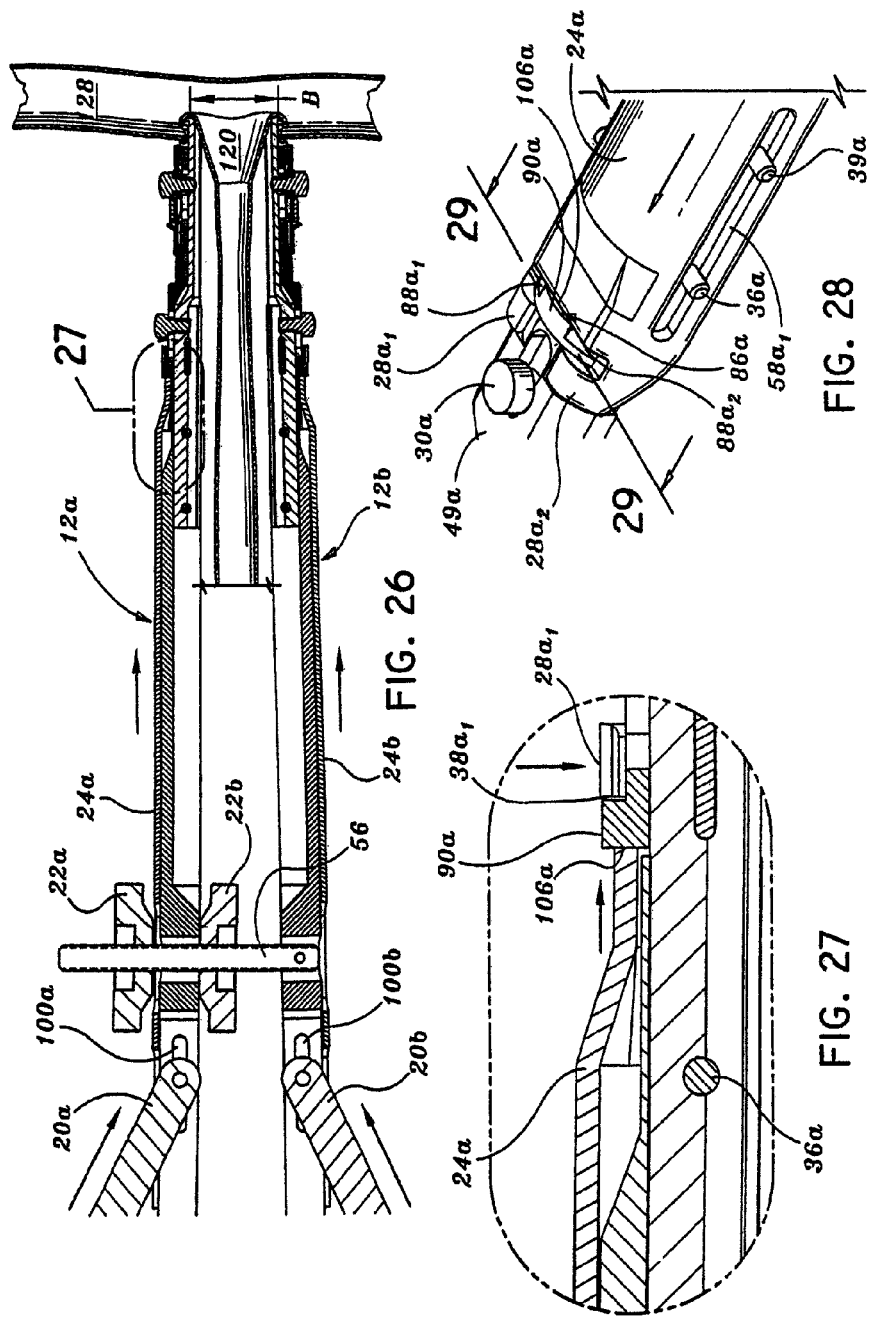

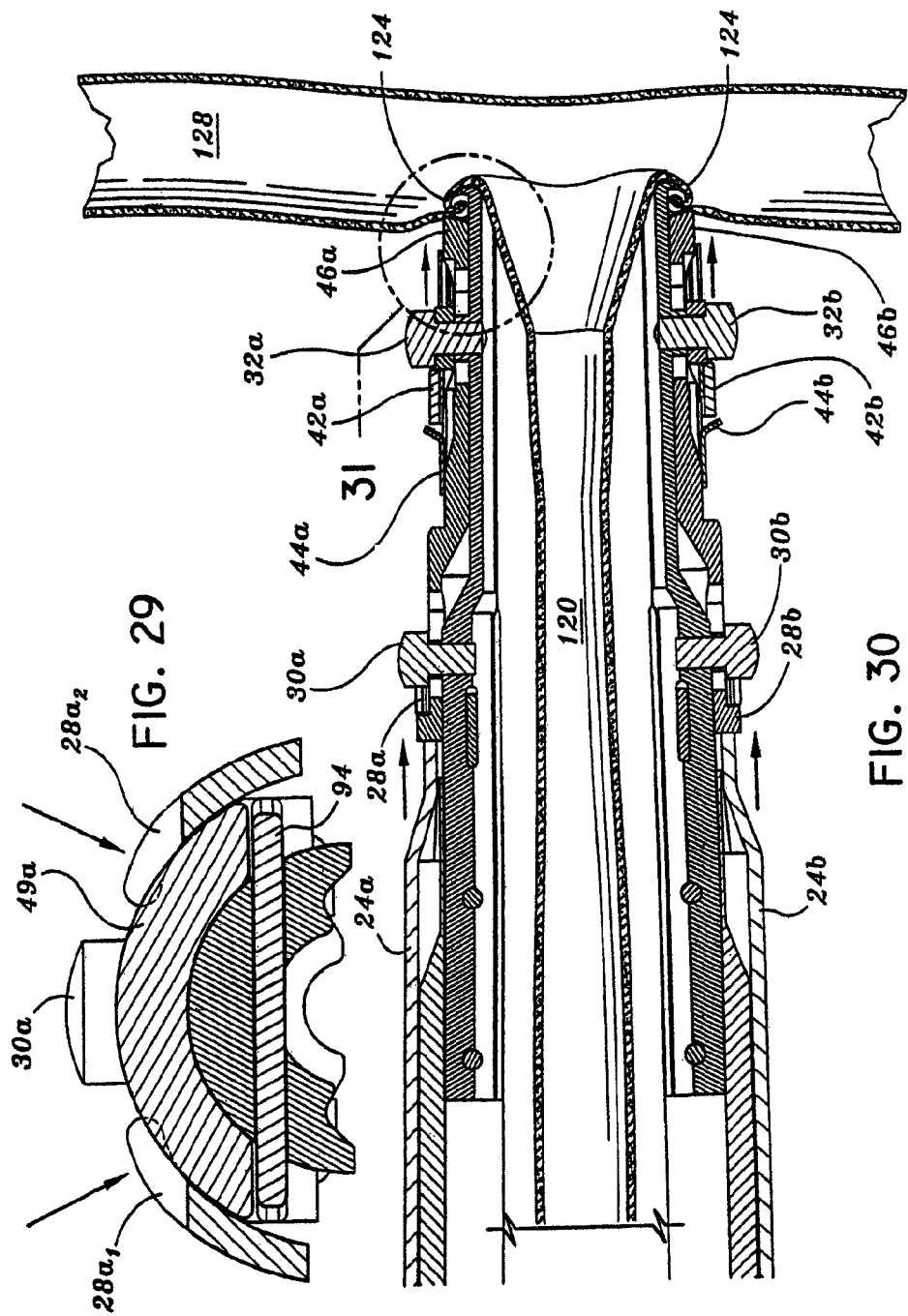

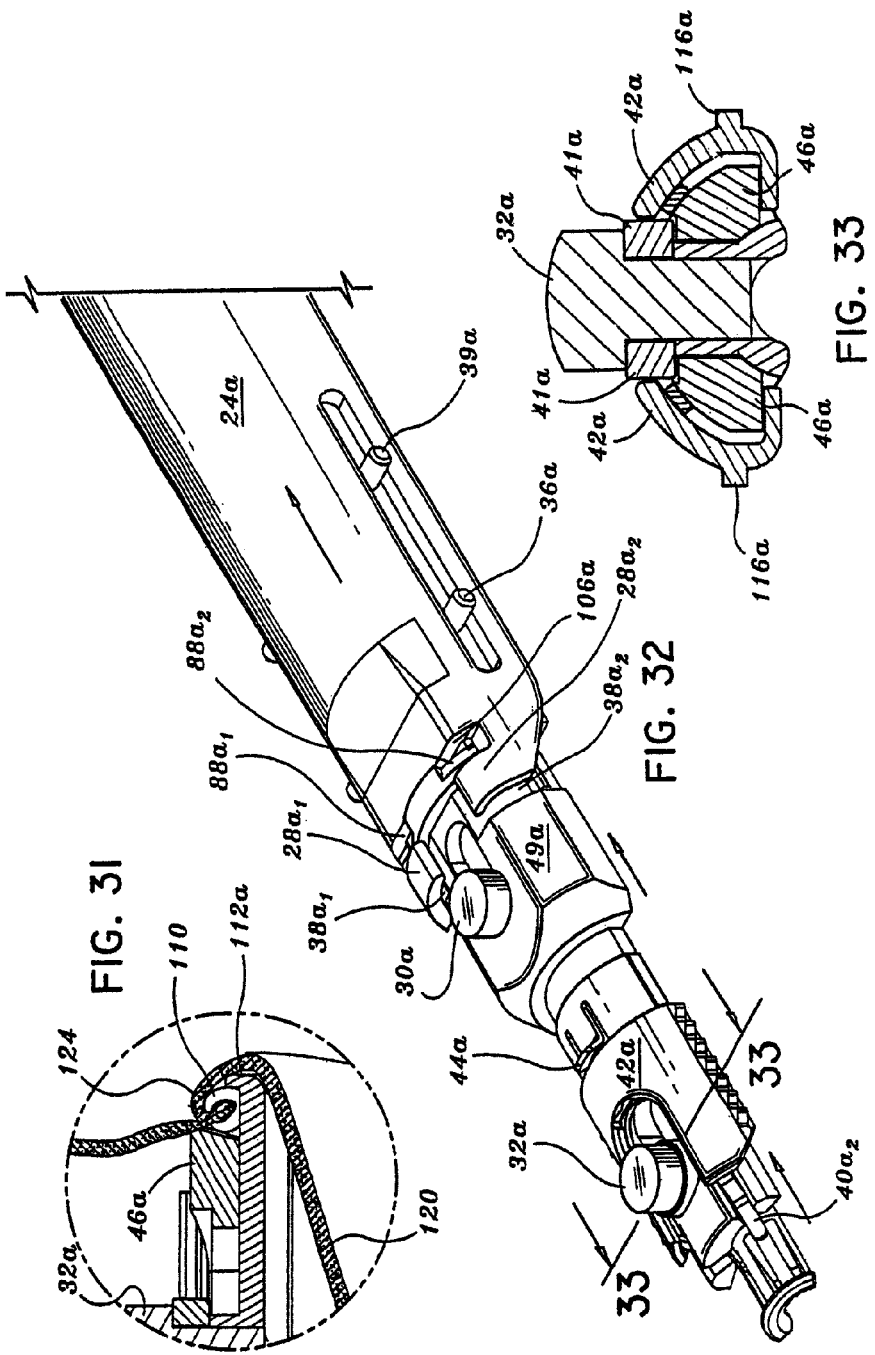

ANASTOMOSIS INSTRUMENT AND METHOD FOR PERFORMING SAME

CROSS REFERENCE TO RELATED APPLICATIONS

This application is a continuation of U.S. patent application Ser. No. 12/203,964 filed Sep. 4, 2008, now U.S. Pat. No. 8,025,198, which is a continuation of U.S. patent application Ser. No. 11/300,101 filed Dec. 13, 2005, now U.S. Pat. No. 7,422,137, which is a continuation of application Ser. No. 10/182,215 filed Jul. 25, 2002, now U.S. Pat. No. 7,223,273, which is a 35 U.S.C. §371 National Filing of PCT/US01/02043 filed Jan. 18, 2001, which claims benefit of U.S. Provisional Application Ser. No. 60/176,697 filed Jan. 18, 2000. Each of these applications is incorporated herein in their entirety by this reference.

BACKGROUND

1. Technical Field

The present disclosure relates to a surgical instrument and method for performing anastomosis of tubular body structures, and more particularly to an instrument for joining vascular tissues, for example, during coronary artery bypass graft procedures.

2. Background of Related Art

Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and/or by modifications in behavior and diet. In other cases, dilatation of coronary arteries may be achieved by such procedures as angioplasty, laser ablation, atherectomy, catheterization, and intravascular stents.

For certain patients, a coronary artery bypass graft ("CABG") is the preferred form of treatment to relieve symptoms and often increase life expectancy. A CABG procedure consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion. Alternatively, the internal mammary artery ("IMA") located in the thoracic cavity adjacent the sternum is likewise suitable for grafting to a coronary artery, such as the left anterior descending artery ("LAD").

The performance of a CABG procedure typically requires access to the heart, blood vessels and associated tissue. Access to the patient's thoracic cavity may be achieved in an open procedure by making a large longitudinal incision in the chest. This procedure, referred to as a median sternotomy, requires a saw or other cutting instrument to cut the sternum and allow two opposing halves of the rib cages to be spread apart.

U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extensive and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating "window". The retractor includes a rigid frame and a translation frame slideably connected to the rigid frame. Lower and upper blades are rotatably mounted to the rigid frame and the translation frame respectively. The "window" approach enables the surgeon to gain access through a smaller incision and with less displacement of the ribs, and consequently, less trauma to the patient.

Once access to the thoracic cavity has been achieved, surgery on the heart may be performed. Such procedures typically require that the heartbeat be arrested while maintaining circulation throughout the rest of the body. Cardioplegic fluid, such as potassium chloride (KCl) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta.

Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is complicated procedure requiring that the desired vessels be properly located and accessed. The progression of the guide wires and catheters must be closely monitored to determine proper placement. Furthermore, the introduction of catheters form punctures in the blood vessels that must be subsequently closed, and there is an increased risk of trauma to the interior walls of the vessels in which the catheters must pass.

Alternatively, the CABG procedure may be performed while the heart is permitted to beat. Such a procedure is now commonly referred to as minimally invasive direct coronary artery bypass (MIDCAB). A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform a CABG procedure, the harvested vessel segment, such as the IMA, is grafted to the coronary artery by end-to-side anastomosis. Typically, sutures are used to graft the vessel segments. However, conventional suturing is complicated by the use of minimally invasive procedures, such as the window approach, e.g., limited access and reduced visibility to the surgical site may impede the surgeon's ability to manually apply sutures to a graft. Additionally, it is difficult and time consuming to manually suture if the CABG procedure is being performed while the heart is beating as the suturing must be synchronized with the heart beat.

As can be appreciated, the process of manually suturing the harvested vessel segment to a coronary artery is time consuming and requires a great deal of skill on the part of the surgeon. The resulting sutured anastomosis will also be dependent on the skills of the surgeon. In minimally invasive procedures such as in MIDCAB, the ability to suture is even more complicated due to limited maneuverability and reduced visibility. U.S. Pat. No. 5,707,380 to Hinchliffe et al., the entire contents of which are hereby incorporated by reference, discloses an apparatus and a procedure that enable remote anastomosis without piercing of vessels during both conventional and minimally invasive procedures. A continuing need exists, however, for improved surgical instruments and methods for performing remote anastomoses during both conventional and minimally invasive procedures.

SUMMARY

The present disclosure relates to a surgical instrument for creating an anastomosis which includes a housing having a handle which extends therefrom and a fastener support member which extends distally from the housing. The fastener support member is configured and dimensioned to releasably support a plurality of surgical fasteners. The surgical instrument also includes a tissue retaining mechanism having a clip which is selectively movable from a first position relative to the fastener support member to a second position in closer proximity with the fastener support member such that tissue disposed adjacent the fastener support member is retained thereagainst. A fastener firing mechanism is also included with the surgical instrument and includes a pusher member which is relatively movable in response to actuation of the handle to simultaneously deform the plurality of surgical fasteners.

Preferably, the housing includes a pair of opposed housing portions each having a distal end which is movable toward and away from each other to define an approximation distance therebetween. An approximation control mechanism may be operatively associated with the first and second opposing housing portions. The approximation control preferably includes a standoff member which connects the first and second housing portions and an approximation adjusting member which engages the standoff member. It is contemplated that one of the first and second opposed housing portions is movable relative to the other opposed housing portions in response to movement of the adjusting member with respect to the standoff member. A locking member may also be included which engages the standoff member and locks the relative approximation distance between the first and second opposed housing portions to a desired approximation distance prior to firing.

In one embodiment, the tissue retaining mechanism includes an actuating sleeve for moving the clip from the first position to the second position. Preferably, a lock member is included with the tissue retaining mechanism to retain the actuating sleeve and the clip in the second position.

In another embodiment, a piston engages the pusher member after activation of the handle such that, upon release of the handle, both the fastener member and the pusher member retract proximally. Preferably, the lock member retains the actuating sleeve and the clip in the second position and also frictionally retains the actuating sleeve and the clip atop the fastener support member such that the actuating sleeve and the clip retract proximally with the fastener support member upon release of the handle.

In yet another embodiment of the present disclosure, an actuator is coupled to the handle and controls both the fastener firing mechanism and the approximation of opposing housing portions.

In still yet another embodiment, the surgical instrument includes a housing having a fastener support member attached thereto which is configured and dimensioned to releasably retain a plurality of surgical fasteners. An actuating assembly is actively associated with the fastener support member to facilitate deformation of at least a portion of the surgical fasteners and a tissue retaining mechanism is selectively operable to retain tissue adjacent the surgical fasteners prior to deformation. Preferably, the surgical fasteners are arranged in an array-like manner on the fastener support member.

In one embodiment, the tissue retaining mechanism includes an actuating sleeve and at least one tissue clip which are moveable from a first position wherein the actuating sleeve and the tissue clips are relative the surgical fasteners to a second position wherein the actuating sleeve and the tissue clips are in closer proximity to the surgical fasteners. The actuating assembly is attached at one end to a handle and attached at an opposite end to a pusher member which is mounted to the fastener support member such that movement of the actuating assembly will reciprocate movement of the pusher member which will, in turn, reciprocate movement to the fastener support member to deform at least a portion of the surgical fasteners. Preferably, the fastener support member includes a firing piston which engages and couples with the pusher member upon activation of the actuating assembly and a hammer portion. The hammer portion is preferably dimensioned to closely abut each of the surgical fasteners to deform at least a portion of the surgical fasteners upon movement of the actuating assembly.

A hammer capture may be incorporated with the firing piston such that upon activation of the actuating assembly, the pusher hammer engages the hammer capture and locks the pusher member to the firing piston and upon release of the actuating assembly, both the pusher member and the firing piston retract proximally.

The present disclosure also relates to a method of performing a vascular anastomosis which includes the steps of:
  a) providing a surgical instrument which includes:
    an upper portion and a lower portion, each of the portions having a fastener support member mounted thereon which is configured and dimensioned to retain a plurality of surgical fasteners;
    an actuating assembly which couples to one of the portions and cooperates with the fastener support members to deform at least a portion of the surgical fasteners;
  b) everting a first end of a first vessel over a distal end of one of the fastener support members such that the first end of the first vessel engages the surgical fasteners retained thereon;
  c) everting a second end of a first vessel over a distal end of the other of the fastener support member such that the second end of the first vessel engages the surgical fasteners retained thereon;
  d) inserting the distal end of both of the fastener support members into an opening in a side wall of a second vessel;
  e) engaging the side wall of the second vessel with the surgical fasteners adjacent the opening;
  f) actuating the actuating assembly to cooperate with the fastener support member to deform the surgical fasteners to secure the first and second vessels together in fluid communication with one another.

Preferably, the method further includes the step of approximating the distance between the two opposing portions relative to the size of the opening of the first vessel prior to insertion of the first vessel into an opening in a side wall of a second vessel.

In one method, after the second everting step, the method further includes the step of positioning the fastener support member of the upper and lower portions in a longitudinally offset manner such that an angle is created relative to the transverse plane of the two portions prior to insertion of the first vessel into an opening in a side wall of a second vessel.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

An illustrative embodiment of the subject surgical instrument and method are described herein with reference to the drawings wherein:

FIG. 19 is a view of an incision formed in the LAD;

FIG. 20 is a horizontal cross-sectional view of the distal end of the surgical fastener support member showing the clamped non-approximated IMA tissue being inserted into the incision of FIG. 19;

FIG. 21 is an enlarged view of the indicated area of detail of FIG. 20;

FIG. 22 is a view similar to FIG. 21, which shows the IMA being expanded within the incision of the LAD as the handles are released and also showing the lower locking dial positioned against the upper portion to lock the upper and lower portions with respect to one another;

FIG. 23 is an enlarged view of the indicated area of detail of FIG. 22 at the point of insertion;

FIG. 26 is a view similar to FIG. 21 during firing of the instrument and showing actuating bars translating reciprocating longitudinal movement to the pusher member;

FIG. 27 is an enlarged, cross-sectional view of the indicated area of detail of FIG. 26 at the point of engagement of the pusher member and the upper anvil;

FIG. 28 is a partial perspective view of the pusher member urging the anvil distally towards the surgical fasteners;

FIG. 29 is an enlarged, cross-sectional view taken along section line 29-29 in FIG. 28;

FIG. 30 is a horizontal cross-sectional view of the distal end of the instrument showing the pusher members biasing the surgical fasteners toward the anvils of the upper and lower portions and deforming the surgical fasteners to attach the IMA to the LAD;

FIG. 31 is an enlarged, cross-sectional view of the indicated area of detail of FIG. 30;

FIG. 32 is a partial perspective view of the surgical instrument after firing showing the co-operative retraction of the fastener support member and the pusher member;

FIG. 33 is a horizontal cross-sectional view taken along line 33-33 of FIG. 32;

DETAILED DESCRIPTION OF PREFERRED EMBODIMENTS

Figure 1:
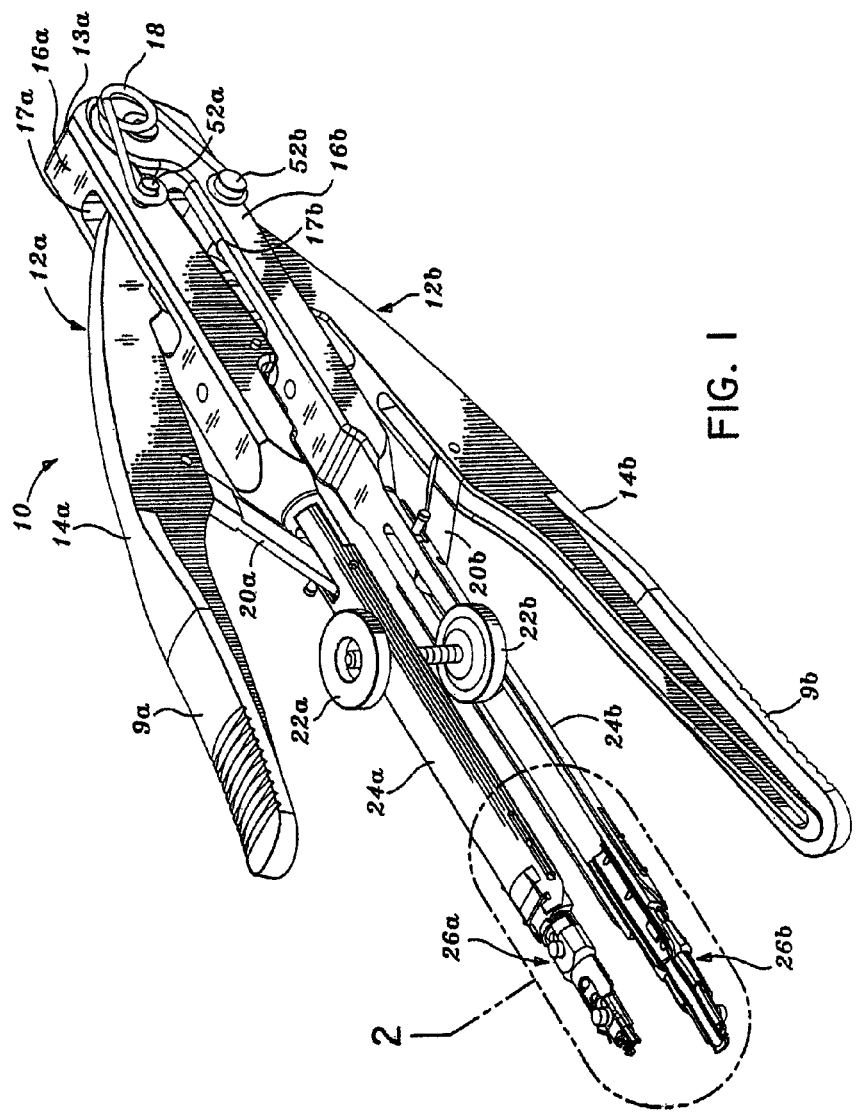
FIG. 1 is a perspective view of a surgical instrument constructed in accordance with a preferred embodiment of the present disclosure.

Preferred embodiments of the surgical instrument and method disclosed herein will be described in terms of a minimally invasive direct coronary artery bypass ("MIDCAB") procedure wherein a vascular anastomosis is created by joining a section of a harvested vessel, e.g., the internal mammary artery ("IMA") or a saphenous vein, to bypass an occlusion in a coronary artery, e.g., the left anterior descending artery ("LAD"). Alternatively, the presently disclosed surgical instrument may also be utilized in performing anastomosis of other tubular luminal body structures.

In the drawings and in the description which follows, the term "proximal", as is traditional, will refer to the end of the apparatus which is closer to the user, while the term "distal" will refer to the end which is further from the user.

Referring now in detail to the drawing figures in which like reference numerals identify similar or identical elements, one embodiment of the present disclosure is illustrated generally in FIG. 1 and is designated therein as surgical instrument 10. Surgical instrument 10 includes a pair of opposing upper and lower portions 12a and 12b, respectively, which include generally symmetrical handle portions 14a and 14b and housings 16a and 16b, respectively. Preferably, handles 14a and 14b are provided with ergonomic surfaces 9a and 9b, respectively, which are contoured and configured to be comfortably gripped by the hands of the user during operation of the instrument.

Since the upper and lower portions 12a, 12b of the surgical instrument 10 are generally symmetrical, the upper opposing portion 12a and the elements described with respect thereto will, hereinafter, be designated with the suffix "a" and the corresponding elements of the lower portion 12b will be designated with the suffix "b".

Figure 2:
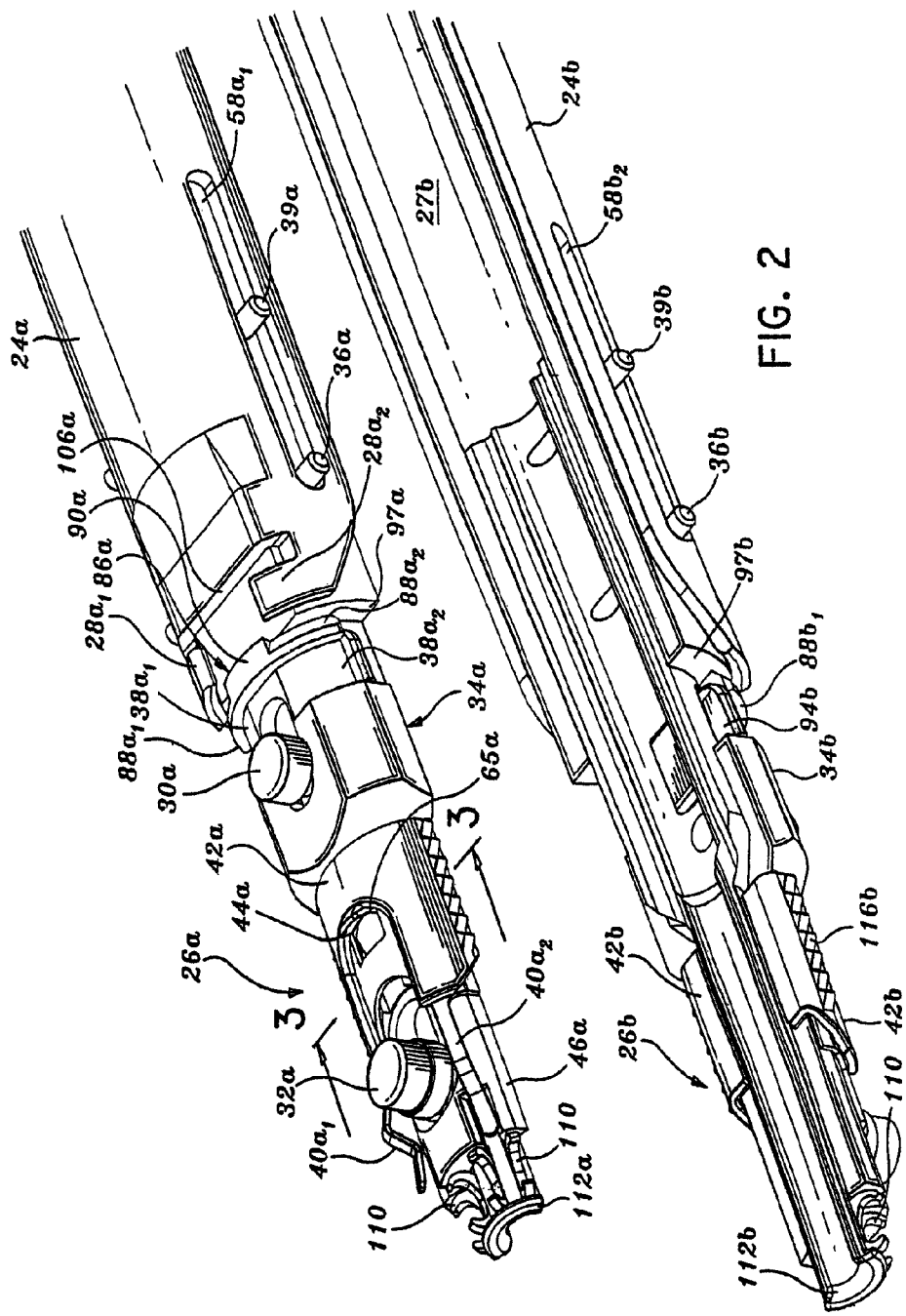
FIG. 2 is an enlarged, partial perspective view of the indicated area of detail of FIG. 1 which shows the upper and lower surgical fastener support members in a retracted, pre-loaded configuration.
Figure 3:
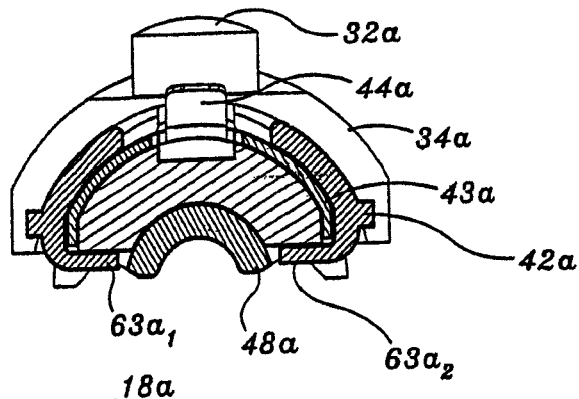
FIG. 3 is a cross-sectional view of the upper surgical fastener support member taken along section line 3-3 of FIG. 2.
Figure 4:
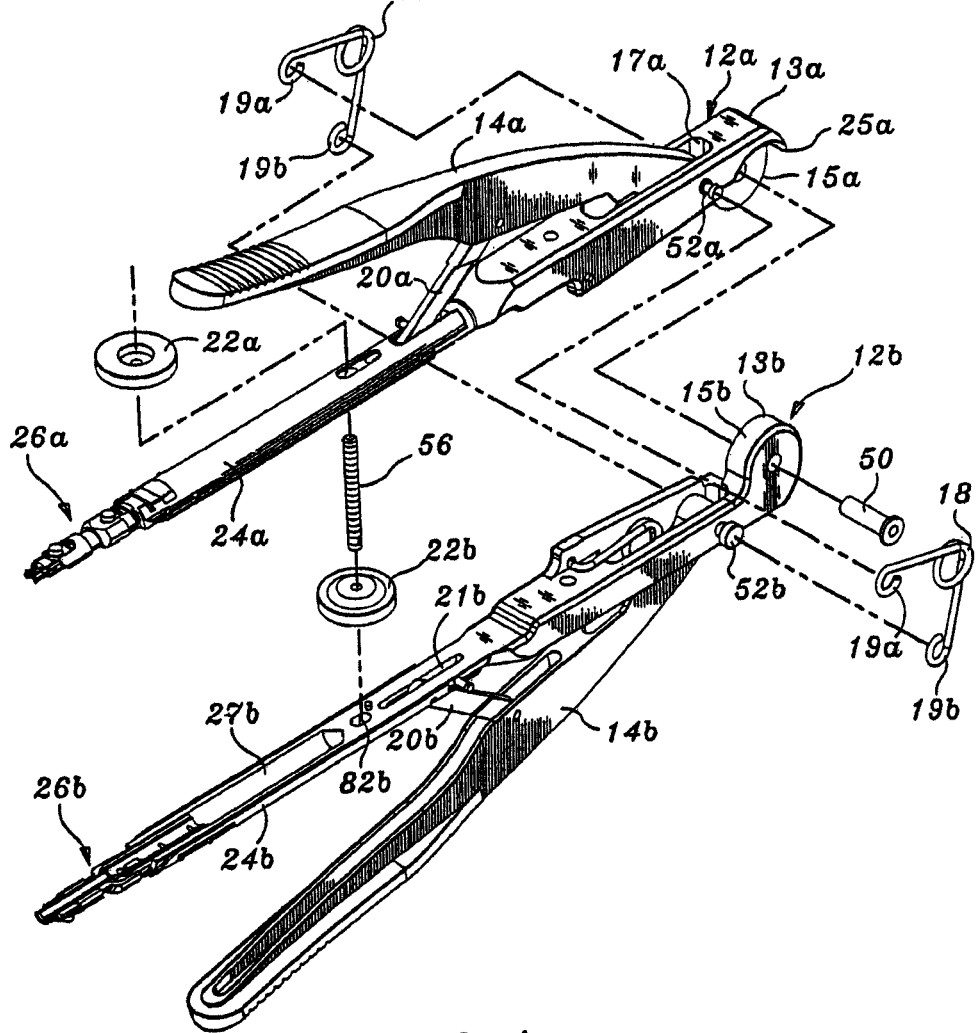
FIG. 4 is a perspective view with parts separated of the surgical instrument of FIG. 1.

As shown in FIGS. 1-5, upper portion 12a and lower portion 12b are attached at their proximal ends by pin 50 which permits pivotal movement of the upper portion 12a with respect to the lower portion 12b about pin 50 (see FIG. 4). Preferably and as best seen in FIG. 4, the proximal end 13a of housing 16a and the proximal end 13b of housing 16b matingly engage one another about pin 50.

Upper portion 15b of proximal end 13b is semi-circular in shape and the upper portion of proximal end 13a is correspondingly dimensioned as an annular flange 25a which matingly receives portion 15b of proximal end 13b. Similarly, the lower portion 25b (see FIG. 8) of end 13b is also annular in shape so as to matingly receive portion 15a when the instrument 10 is assembled.

Housing 16a also includes a longitudinal handle slot or channel 17a located therein which extends from the proximal end 13a of housing 16a towards the distal end of the same. Preferably, handle 14a is received within slot 17a and is pivotally secured within housing 16a by pin 52a. Likewise, pin 52b pivotally secures handle 14b within slot 17b of housing 16b. As best illustrated in FIG. 4, pins 52a and 52b perform an additional function, i.e., the outer ends of each pivot pin 52a, 52b protrude outwardly from the side of each housing 16a, 16b, such that pivot pins 52a, 52b also act as bosses for torsion springs 18 when the upper portion 12a and lower portion 12b are matingly engaged. More particularly, a pair of loop ends 19a, 19b formed on torsion springs 18 are sufficiently dimensioned to encircle pins 52a, 52b, respectively.

Figure 5:
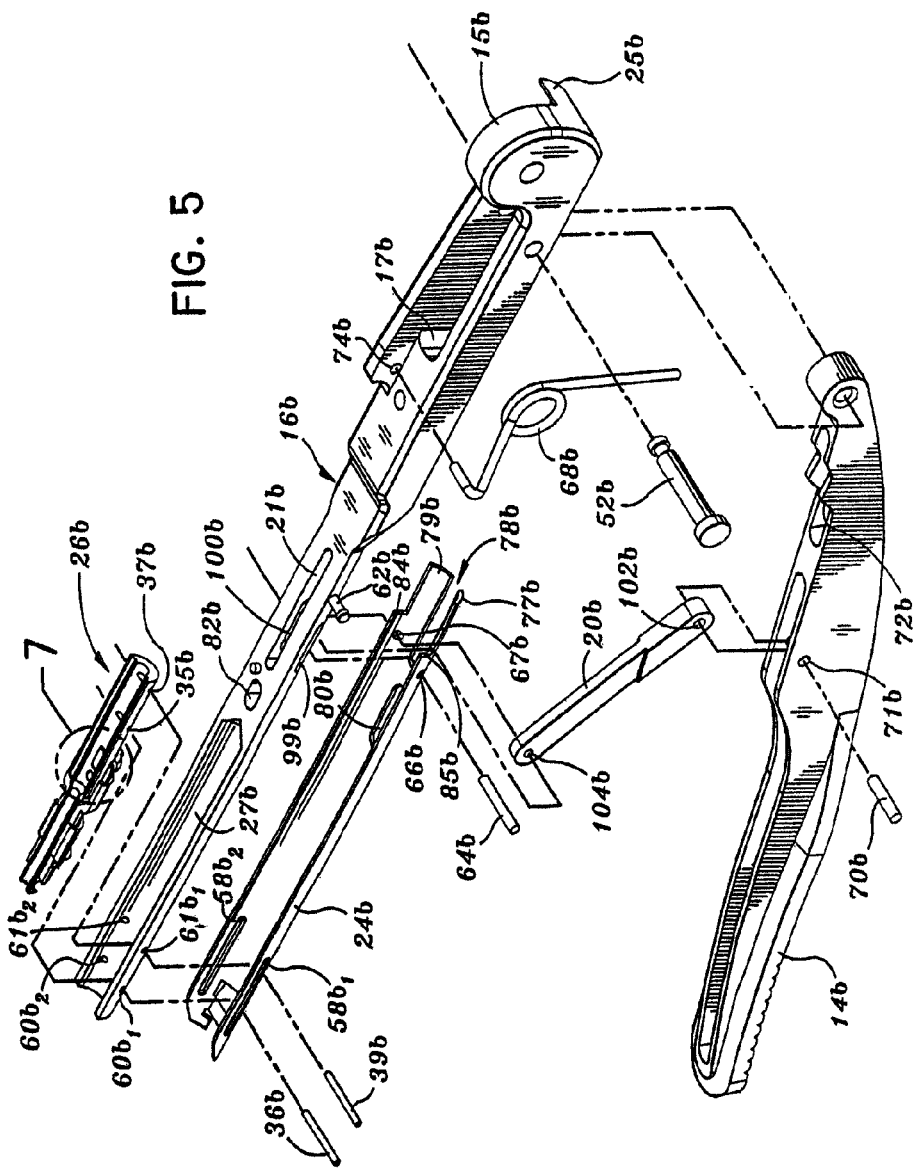
FIG. 5 is a perspective view with parts separated of the lower portion of the surgical instrument.

As depicted in FIG. 5, housing 16b further includes a second slot or channel 21b which is dimensioned to slidingly receive an actuating link bar 20b therein. Actuating link bar 20b is pivotably affixed at its proximal end to handle 14b by pin 70b which locks bar 20b in place within handle 14b. More particularly, actuating link bar 20b has an aperture 102b which aligns with aperture 71b of handle 14b when bar 20b is affixed to handle 14b. Pin 70b is inserted through apertures 71b and 102b to affix link bar 20b to handle 14b.

The distal end of actuating link bar 20b is slidingly received within slot 21b and slideably affixed to the housing 16b by slide pin 64b through a pair of parallel side channels 99b and 100b (see also FIG. 8) which are each located in spaced relation within slot 21b. Slide pin 64b also affixes a pushing member 24b to the distal end of the actuating link bar 20b, which will be explained in greater detail below.

Housing 16b also includes a second torsion spring 68b which is affixed at one end to housing 16b through an aperture 74b and biased at the opposite end against a proximal portion of handle 14b, e.g., spring bias block 72b. Spring 68b encourages movement of the housing 16b and the handle 14b in an opposing manner with respect to one another while the actuating link bar 20b which is attached between the housing 16b and the handle 14b limits the overall distance of the opposing movement between the two members 14b and 16b.

As mentioned above, pusher member 24b is also affixed to the distal end of the actuating link bar 20b by slide pin 64b. Preferably, the proximal end of pusher member 24b is bifurcated to form prongs 77b and 79b which, together, define a slot 78b therebetween. Each prong 77b and 79b includes a stepped portion 85b and 84b, respectively, which cooperate to limit proximal movement of the pusher member 24b, which will be described in further detail below. Pusher member 24b also includes a pair of opposing apertures 66b and 67b located distally of stepped portions 84b, 85b and sufficiently dimensioned to receive slide pin 64b. As shown in FIG. 5, the inner face of pusher member 24b is preferably concave and dimensioned to matingly engulf and couple to the outer surface of the housing member 16b in a slide-like manner.

During assembly of the surgical instrument 10, pusher member 24b is slideably coupled to the outer surface of housing 16b such that slot 78b and slot 21b reside in general vertical alignment with one another. Preferably, stepped portions 84b, 85b are positioned on the distal side of a stop 62b which is affixed to a side of housing 16b so as to limit proximal movement of the pusher member 24b with respect to housing 16b and, in turn, limit the distance between handle 14b and housing 16b. Actuating link bar 20b is positioned within both slot 78b and side channel 100b. Slide pin 64b is inserted through aperture 66b, through housing side channel 99b, through aperture 104b of actuating link bar 20b, through side channel 100b and through aperture 67b to lock actuating link bar 20b to pusher member 24b and slideably lock pusher member 24b within side channels 99b and 100b of housing 16b.

As can be appreciated, relative longitudinal movement of actuating link bar 20b is limited by the proximal and distal ends of side channels 99b and 100b and, in turn, the longitudinal movement of the pusher member 24b is controlled by actuating link bar 20b. As mentioned above, proximal movement of the pusher member 24b is also limited due to stepped portion 85b abutting stop 62b.

FIGS. 4 and 5 also show the relative position of a pair of locking dials 22a and 22b with respect to upper and lower portions 12a and 12b. Preferably, a first end of a standoff member 56 is designed to fit through a pair of vertically aligned apertures 80b and 82b formed in the pusher member 24b and the housing 16b, respectively. The second end of standoff member 56 is designed to fit through another pair of vertically aligned apertures 80a and 82a located in pusher member 24a and housing 16a, respectively (see FIG. 8).

As illustrated best in FIG. 4, locking dial 22b threadably engages standoff member 56 and is disposed between upper and lower portions 12a and 12b. Locking dial 22a which also threadably engages standoff 56 is disposed between the upper portion 12a and handle 14a. Orienting the locking dials 22a and 22b in this fashion allows a user to approximate the expanded size of the IMA 120 prior to inserting the IMA into the LAD 128 (see FIG. 18) and lock portions 12a and 12b with respect to one another to initiate firing of the instrument 10 as will be explained in greater detail below with respect to FIGS. 16 and 17.

Figure 8:
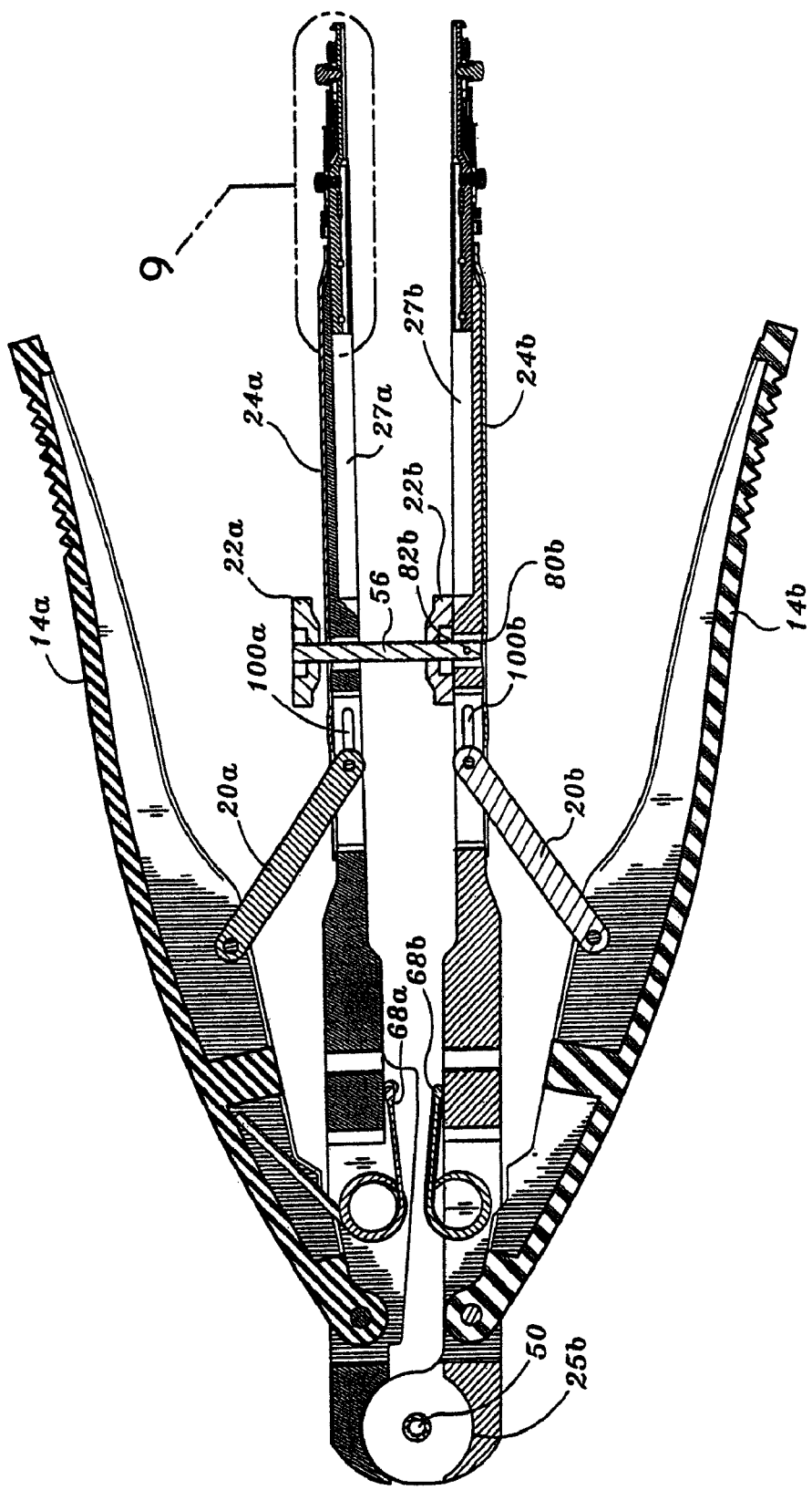
FIG. 8 is a horizontal cross-sectional view of the surgical instrument of FIG. 1.

As best seen in FIGS. 5 and 8, housing members 16a and 16b also include carriage portions 27a, 27b, located at their respective distal ends. More particularly, FIG. 5 shows carriage portion 27b located distally of aperture 82b on housing member 16b. Preferably, the inner surface of carriage 27b is concave and sufficiently dimensioned to receive surgical fastener support member 26b the outer surface of which is generally convex. Pins 36b and 39b affix the distal end of fastener support member 26b within carriage 27b. More particularly, pin 36b is inserted through slot 58b1 of pusher member 24b and then through apertures 60b1 disposed on one side of the carriage 27b and also through slot 35b which extends through the sides of the fastener support member 24b. Pin 36b then extends through aperture 60b2 which is disposed on the opposite side of carriage 27*b* and then through slot 58*b*2 to slideably couple the distal end of the fastener support member 26*b* within carriage 27*b*.

In much the same fashion, pin 39*b* affixes the proximal end of the fastener support member 26*b* to the carriage 27*b* through slot 58*b*1 and apertures 61*b*1, 37*b*, 61*b*2, respectively, and lastly through slot 58*b*2 to slideably engage the proximal end of the fastener support member 26*b* to carriage 27*b*. As best seen in FIG. 5, pins 36*b*, 39*b* are inserted through channels 58*b*1 and 58*b*2 located on opposing sides of the pusher member 24*b* and slideably attach the pusher member 24*b* to the housing 16*b* which also facilitates slideable movement of the pusher member 24*b* with respect to the housing 16*b*.

Figure 6:
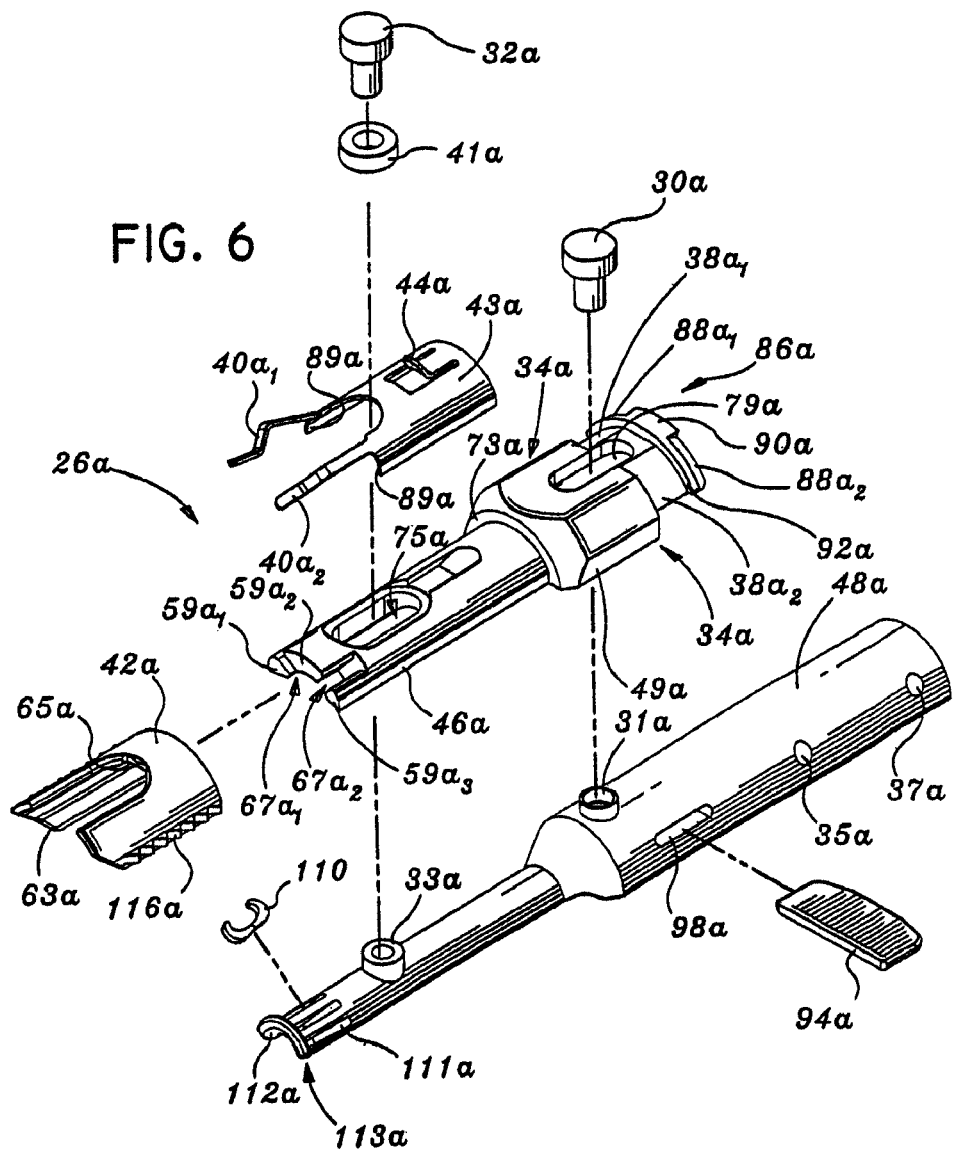
FIG. 6 is a perspective view with parts separated of a surgical fastener support member.

Turning now in detail to FIGS. 2 and 6 which show one preferred embodiment of the fastener support members 26*a* and 26*b*. Fastener support member 26*a* includes a firing piston 34*a* having a hammer portion 46*a* located at the distal end thereof, a semi-annular rim 86*a* located at the proximal end thereof and an anvil 49*a* located therebetween. The proximal end of the semi-annular rim 86*a* has a pair of cammed surfaces 88*a*1 and 88*a*2 and the distal end of the semi-annular rim 86*a* has a stepped semi-annular surface 92*a*.

Preferably, the hammer portion 46*a* of the firing piston 34*a* is generally arcuately shaped and includes three prongs 59*a*1, 59*a*2, and 59*a*3 and, therefore, a pair of slots 67*a*1 and 67*a*2 are formed between the three hammer prongs 59*a*1, 59*a*2, 59*a*3, respectively.

A tissue clamping clip 43*a* is slideably coupled to the distal portion of the firing piston 34*a* and is disposed between a distal end 73*a* of the anvil 49*a* and the hammer 46*a*. Advantageously, the inner periphery of the clamping clip 43*a* is concave to facilitate slideable movement atop the firing piston 34*a*. Preferably, the clamping clip 43*a* also includes longitudinally depending side flanges 89*a* which are sufficiently dimensioned to slideably engage the outer periphery of the hammer portion 46*a* of the firing piston 34*a*. Clamping clip 43*a* also includes a lockout flange 44*a* and a pair of flexible, finger-like tissue clamps 40*a*1 and 40*a*2 which are cammed upwardly and distally from the remainder of the clamping clip 43*a*.

As shown best in FIGS. 3 and 6, a U-shaped actuating sleeve 43*a* is sufficiently dimensioned to slideably engage the outer periphery of the clamping clip 43*a*. More particularly, the actuating sleeve 42*a* is preferably concave and each longitudinal side edge thereof includes an inwardly extending side flange 63*a*1 and 63*a*2 which is dimensioned to slideably engage the outer periphery of the clamping clip 43*a* and retain the clamping clip 43*a* atop the firing piston 34*a* (see FIG. 3). When the actuating sleeve 42*a* slides over the distal portions of the tissue clamps 40*a*1, 40*a*2, the tissue clamps 40*a*1, 40*a*2 cam downwardly between slots 67*a*1 and 67*a*2 of the hammer portion 46*a* the purpose of which will be explained in more detail below with respect to the operation of the surgical instrument 10.

Fastener support member 26*a* also includes an anchoring sleeve 48*a* which affixes by way of pins 36*a*, 39*a* to the housing member 16*a* through aperture 35*a* and 37*a* in the manner described above and as best seen in FIG. 6. Preferably, the distal end of sleeve 48*a* is semi-circular and includes a surgical fastener support section 113*a* having a semi-annular array of longitudinal fastener support channels or cradles 111*a* each of which are configured and dimensioned to support a generally "C"-shaped surgical fastener or clip 110 therein by, for example, friction or partial compression of clips 110. Preferably, the longitudinally oriented cradles 111*a* form an eccentric array radially about the outer surface of anchoring sleeve 48*a*. This arrangement serves to form an angled connection or fistula between the vessels to be joined. It has been seen that such a connection may facilitate better fluid flow through the anastomotic site.

Figure 9:
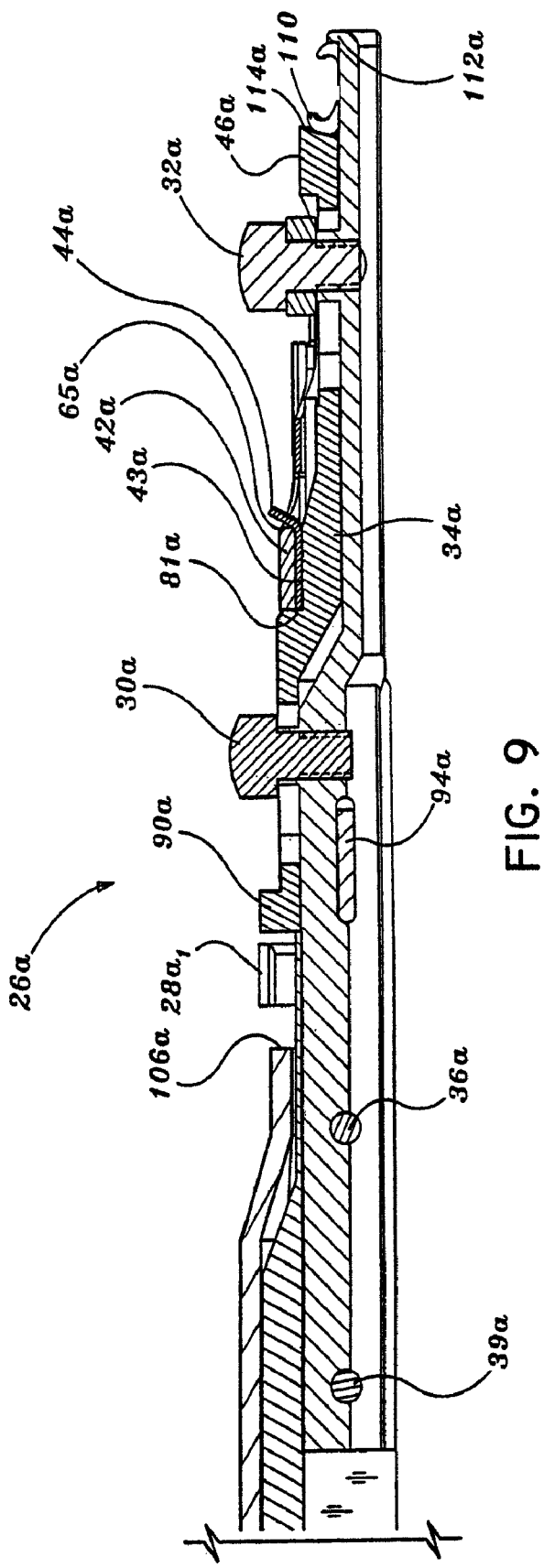
FIG. 9 is an enlarged, horizontal cross-sectional view of the indicated area of detail shown in FIG. 8.
Figure 11:
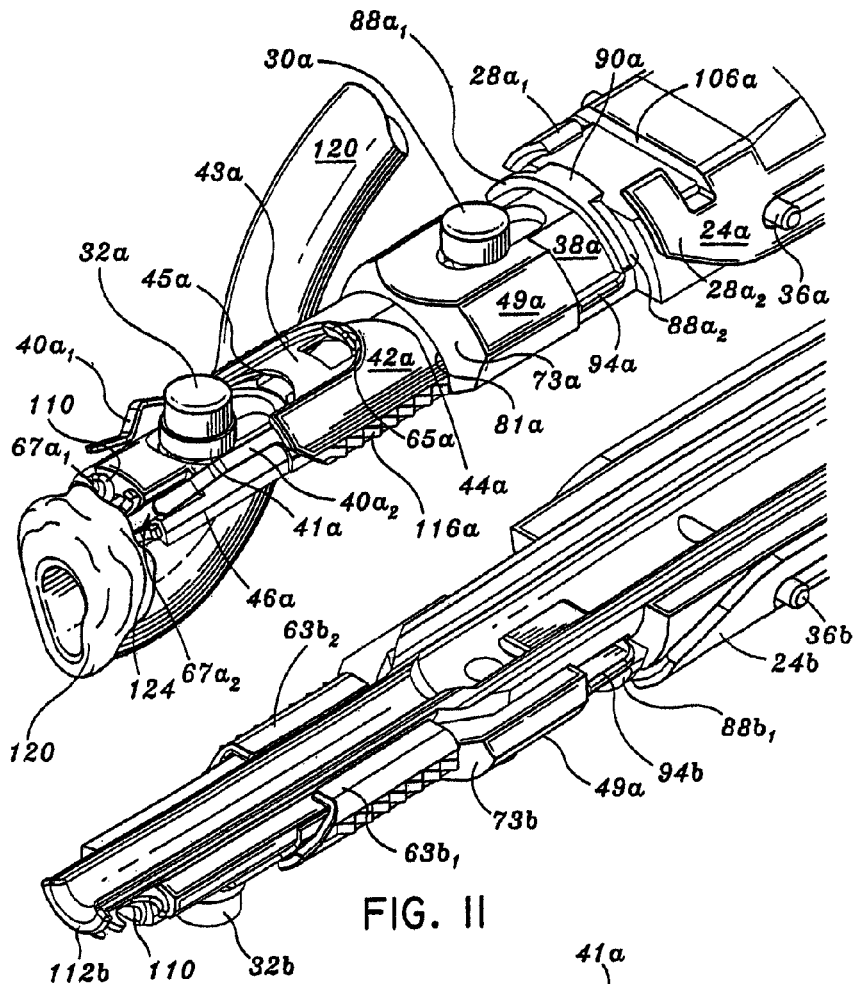
FIG. 11 is an enlarged, partial perspective view of the surgical fastener support member shown with a portion of the IMA everted over a plurality of surgical fasteners with tissue clamping prongs shown in a retracted position.
Figure 12:
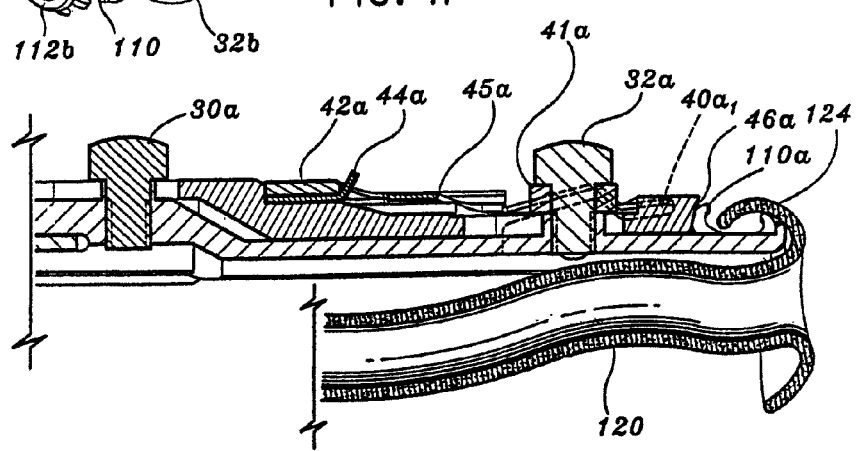
FIG. 12 is a horizontal cross-sectional view of the surgical fastener support member of FIG. 11 shown with an actuating sleeve and a tissue clamp in a retracted position.

As shown in more detail with respect to FIGS. 8, 9, and 11, a single fastener 110 is positioned within each cradle 111*a* so as to closely abut against an anvil 112*a* which is radially disposed at the distal-most end of the anchor sleeve 48*a*. Once assembled, the hammer portion 46*a* of the firing piston 34*a* closely abuts against the opposite end of each fastener 110 to partially compress each fastener 110 and, therefore, retain each fastener 110 within the respective cradle 111*a*.

When assembled, the U-shaped actuating sleeve 42*a* is engaged atop the firing piston 34*a* with the clamping clip 43*a* frictionally held in position therebetween. The actuating sleeve 42*a* is positioned atop the clamping clip 43*a* in a retracted position such that the inner distal edge 65*a* of the actuating sleeve 42*a* closely abuts the upwardly extending lockout flange 44*a* of the clamping clip 43*a* and the proximal edge 81*a* of the actuating sleeve 42*a* abuts the inner leading edge 73*a* of anvil 49*a* as best seen in FIG. 11. Once assembled, the tissue clamps 40*a*1 and 40*a*2 are preferably positioned in general vertical alignment with slots 67*a*1, 67*a*2, respectively, such that as the tissue clamps 40*a*1, 40*a*2 are cammed downward by movement of the actuating sleeve 42*a* over the clamping clip 43*a*, the tissue prongs 40*a*1 and 40*a*2 descend through slots 67*a*1 and 67*a*2 and clamp the end 124 of the everted tissue 120 (see FIG. 15). This will be explained in greater detail below with respect to the operation of the fastener support member 26*a*.

Referring temporarily back to FIG. 6, a post 32*a* and an annular bushing 41*a* are inserted through a slot 75*a* of firing piston 34*a* and held in place by way of an anchoring ring 33*a* located near the distal end of sleeve 48*a*. Post 32*a* in combination with annular bushing 41*a* operate to slideably couple the distal end of firing piston 34*a* to the distal end of anchoring sleeve 48*a*. Firing piston 34*a* is also slideably coupled to anchoring sleeve 48*a* by way of a post 30*a* which is inserted through a slot 79*a* of the firing piston 34*a* and received within a ring 31*a* of anchoring sleeve 48*a*. Preferably, post 30*a* frictionally engages ring 31*a*, however, in some cases it may be preferable to retain post 30*a* within ring 31*a* in some other manner, e.g., glue or snap-fit.

Figure 7:
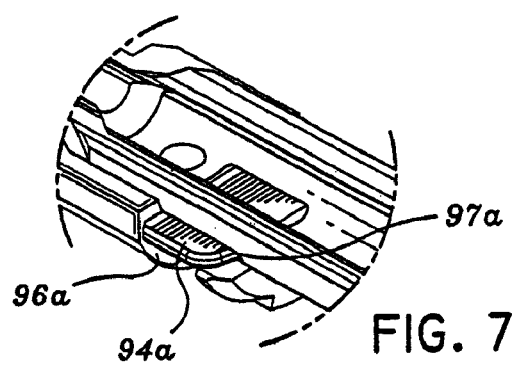
FIG. 7 is an enlarged, partial perspective view of a support tab for the surgical fastener support member.

Once the fastener support member 26*a* is assembled, the surgical fasteners 110 are held in position within cradles 111*a* against annular rim 112*a* by the hammer prongs 59*a*1, 59*a*2 and 59*a*3. More particularly and as best seen in FIGS. 6 and 7, a tab-like stay 94*a* is inserted into a slot 98*a* located within anchoring sleeve 48*a* and is biased against an innermost proximal edge 97*a* of the slot 98*a* so as to urge the rear end 96*a* of the firing piston 34*a* forward into firing position, i.e., the hammer prongs 59*a*1-59*a*3 are urged distally to abut the proximal end of the surgical fasteners 110 and partially compress each fastener 110, thereby retaining each fastener 110 within its respective cradle 111*a*.

In use and as shown in FIGS. 8-35, surgical instrument 10 facilitates the performance of a vascular anastomosis and either eliminates and/or minimizes the need for manual suturing of the vessels. The method and usage described herein will be addressed in terms of minimally invasive vascular anastomosis performed on a beating heart such as in a MID-CAB procedure. However, the presently disclosed surgical instrument 10 may also be used in performing anastomoses of other tubular or luminal body structures without departing from the scope of the present disclosure. For example, surgical instrument 10 may be used in conventional open CABG procedures using a median sternotomy or other large incision without stopping the heart. Alternatively, the thoracic "window" procedure may be used to achieve access to the heart. The "window" approach involves a smaller incision and less displacement of the ribs, and therefore is less traumatic to the patient. For this approach, conventional surgical techniques are used to determine the location of the incision to access the chest cavity.

Figure 10:
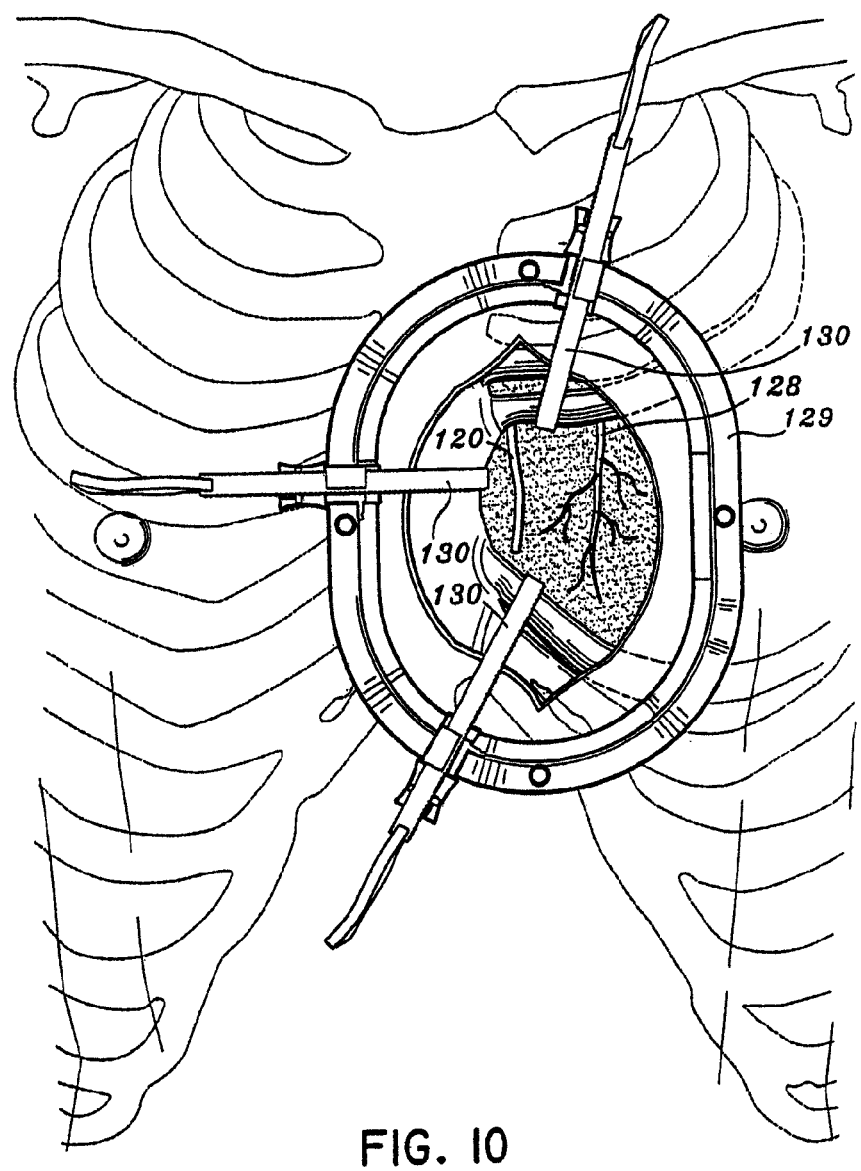
FIG. 10 is a plan view of a surgical retractor assembly placed on a patient's chest to provide access to the heart.

To gain access to the heart, after an incision is made, a surgical retractor assembly may be used to separate the ribs at the site of the incision as shown in FIG. 10. Specifically, a base 129 is placed on the chest of the patient with the central opening defined by the base being positioned over the operative site. Retractor assemblies 130 are mounted to the base 129 at various locations. Each retractor assembly 130 includes a blade having a hook to engage either a rib or the sternum therewith. The retractor assemblies are mounted and used to retract ribs until a sufficiently large opening in the chest cavity is defined to provide direct access to the heart. For example, the sternum and the fourth and fifth ribs can be split apart to create a window. Other configurations of spreading the ribs and/or selectively cutting individual ribs away from the sternum may also be utilized for a particular procedure.

Once the desired access to the heart is achieved, the graft vessel, e.g., the internal mammary artery (IMA) 120 is dissected from the surrounding cartilage and muscle, and a free end of the vessel is exposed. The occluded coronary artery, e.g., the left anterior descending artery (LAD) 128, is then prepared for receiving the IMA 120 graft. The heart is positioned in the desired orientation either by traction sutures passing through the pericardium or by manipulation with heart manipulation instruments which are held by the surgical personnel or clamped in a fixed orientation to a base such as the retractor assembly base. Blood flow through the LAD 128 can be restricted by cardiopulmonary bypass and pericardial cooling. Alternatively, a dampening instrument may be applied directly on the LAD 128 to restrict blood flow and reduce movement of the heart near the LAD.

Turning now in detail to the operation of the surgical instrument 10 and in particular, fastener support member 26a as detailed in FIGS. 11-15, once the IMA 120 has been harvested, the user everts the upper portion (the "toe") of the free end 124 of the IMA 120 over the distal end of the fastener support member 26a such that the free end 124 of the IMA 120 is retained by the distal-most portions of the surgical fasteners 110. Everting of the IMA 120 may be achieved by any suitable known instruments and/or techniques such as by using graspers. With the IMA 120 everted in this fashion, the user then urges the actuating sleeve 42a distally by grasping the side edges 116a of the actuating sleeve 42a. Preferably, the side edges 116a of the actuating sleeve are each formed with a grip-like surface, e.g., a corrugated surface, which facilitates a firm grip during distal movement of the actuating sleeve 42a during operating conditions.

Figure 13:
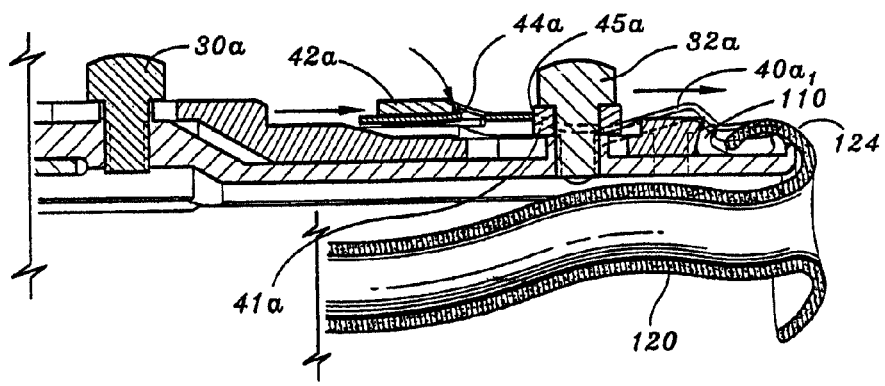
FIG. 13 is a horizontal cross-sectional view of the surgical fastener support member of FIG. 11 showing the actuating sleeve depressing a lockout flange and urging the tissue clamp forward over the everted tissue.
Figure 14:
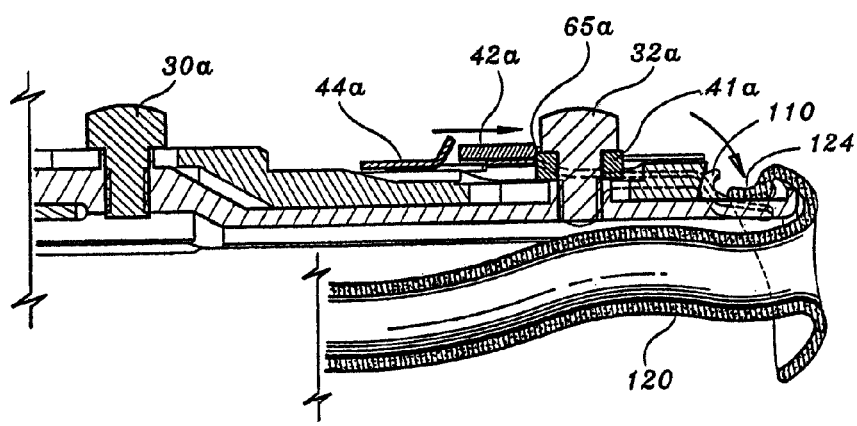
FIG. 14 is a horizontal cross-sectional view of the surgical fastener support member of FIG. 11 showing the actuating sleeve locked into position and the tissue prongs clamped atop the everted tissue.
Figure 15:
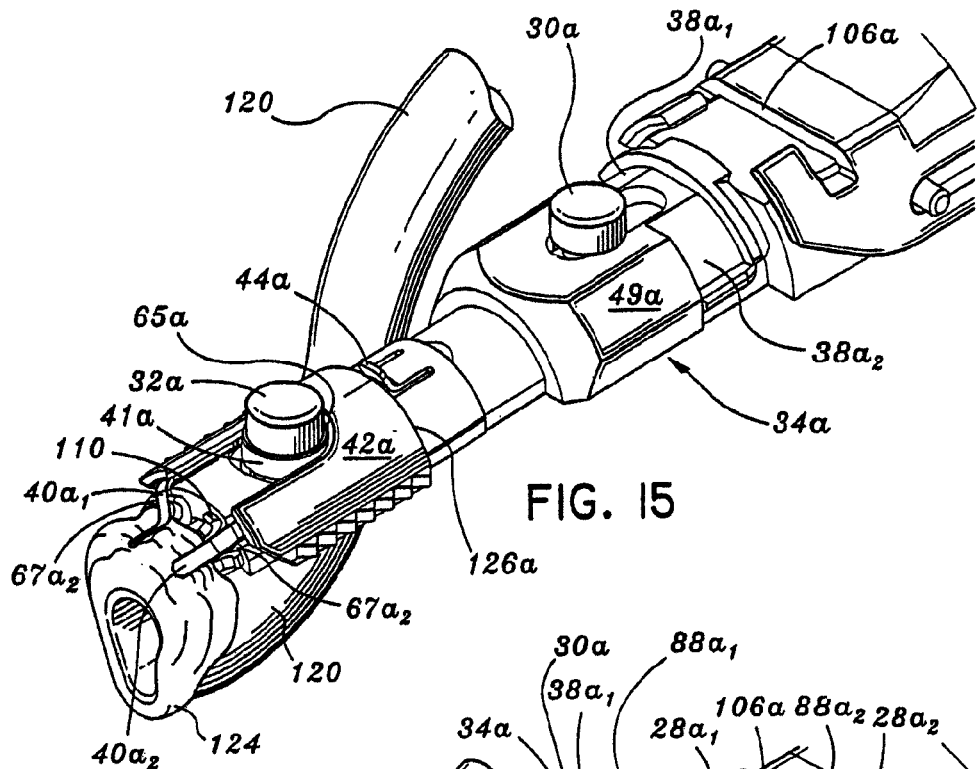
FIG. 15 is an enlarged, partial perspective view of the fastener support member with a portion of the IMA everted over the surgical fasteners with the tissue prongs shown in engaged and clamped position atop the everted tissue.

As shown in FIGS. 13, 14 and 15 when the user initially moves the actuating sleeve 42a forward, both the actuating sleeve 42a and the clamping clip 43a move distally until the forward edge 45a (see FIG. 11) of the clamping clip 43a abuts bushing 41a limiting further distal movement of the clamping clip 43a. Movement of the clamping clip 43a distally against bushing 41a poises the tissue clamps 40a1, 40a2 over the "toe" portion of the everted tissue 124 above apertures 67a1, 67a2. The user continues to urge the actuating sleeve 42a distally over the clamping clip 43a such that the flexible lock out flange 44a is depressed by actuating sleeve 42a and, simultaneously, the distal portion of the actuating sleeve 42a cams tissue prongs 40a1, 40a2 downwardly towards the everted tissue 124 over the surgical fasteners 110 and into apertures 67a1, 67a2 as best seen in FIGS. 13 and 14.

The user continues to move the actuating sleeve 42a distally until inner edge 65a of the actuating sleeve 42a abuts post 32a and flange 44a springs back to its unbiased, neutral position locking the actuating sleeve 42a against post 32a and locking the tissue prongs 40a1, 40a2 in a clamped position atop end tissue 124 as shown in FIGS. 14 and 15.

Figure 18:
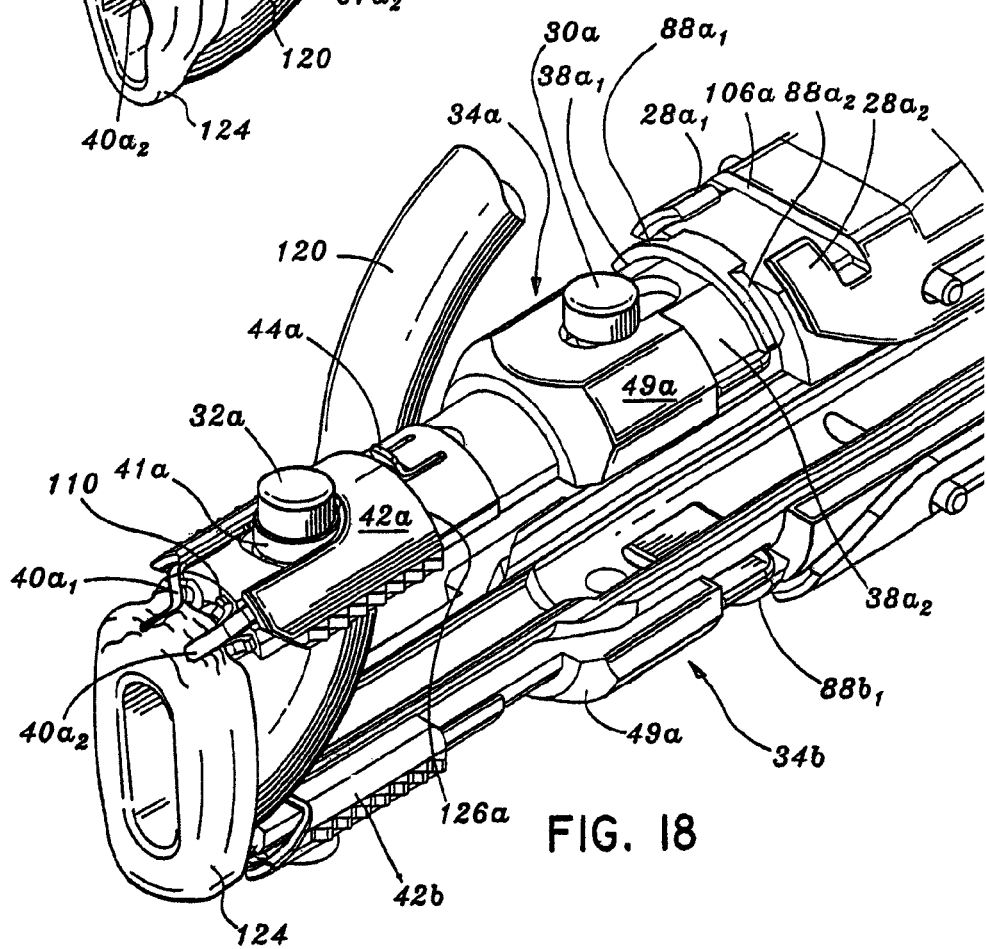
FIG. 18 is partial perspective view of the upper and lower surgical fastener support members shown with the "toe" and "heel" portions of the IMA clamped atop each set of surgical fasteners, respectively.

The user then squeezes the upper and lower handles 14a and 14b, respectively, such that handles 14a and 14b pivot about pivot pin 52a and 52b causing the two fastener support members 26a and 26b to move toward one another. This allows the user to evert the opposite end portion of the IMA 120 (the "heel") over surgical fasteners 110 as shown in FIG. 18. The same procedure noted above is utilized to clamp the "heel" portion of the IMA 120 onto the surgical fasteners 110 utilizing fastener support member 26b, as best seen in FIG. 18.

In some cases it may be preferable to orient the upper and lower portions 12a and 12b in a slightly longitudinally offset manner such that an angle is created relative to the transverse plane of the two portions 12a, 12b in order to optimize the anastomosis and to facilitate optimal blood flow across the graft site from the IMA 120 to the LAD 128. This junction will create a more dramatically visible "heel" and "toe" effect in which an acute or obtuse angle between the vessels is clearly defined.

As can be appreciated from the present disclosure, initially squeezing the 14a, 14b causes the distal ends of the fastener support members 26a and 26b to approximate and does not cause the actuating bars 20a, 20b and pusher members 24a, 24b to slide within slots 99a, 100a and 99b, 100b. This particularly advantageous feature is due to torsion springs 18 having a spring force which is less than the spring force of either handle spring 68a or 68b; and/or upper portion 12a and lower portion 12b being unbiased, i.e., freely movable, with respect to one another.

The remaining portion of the IMA 120 is positioned between the upper and lower portions 12a and 12b, respectively, such that the remaining portion of the IMA 120 is proximally disposed with respect to the instrument 10 thereby facilitating insertion of the IMA 120 into the LAD 128 as described below.

Figure 16:
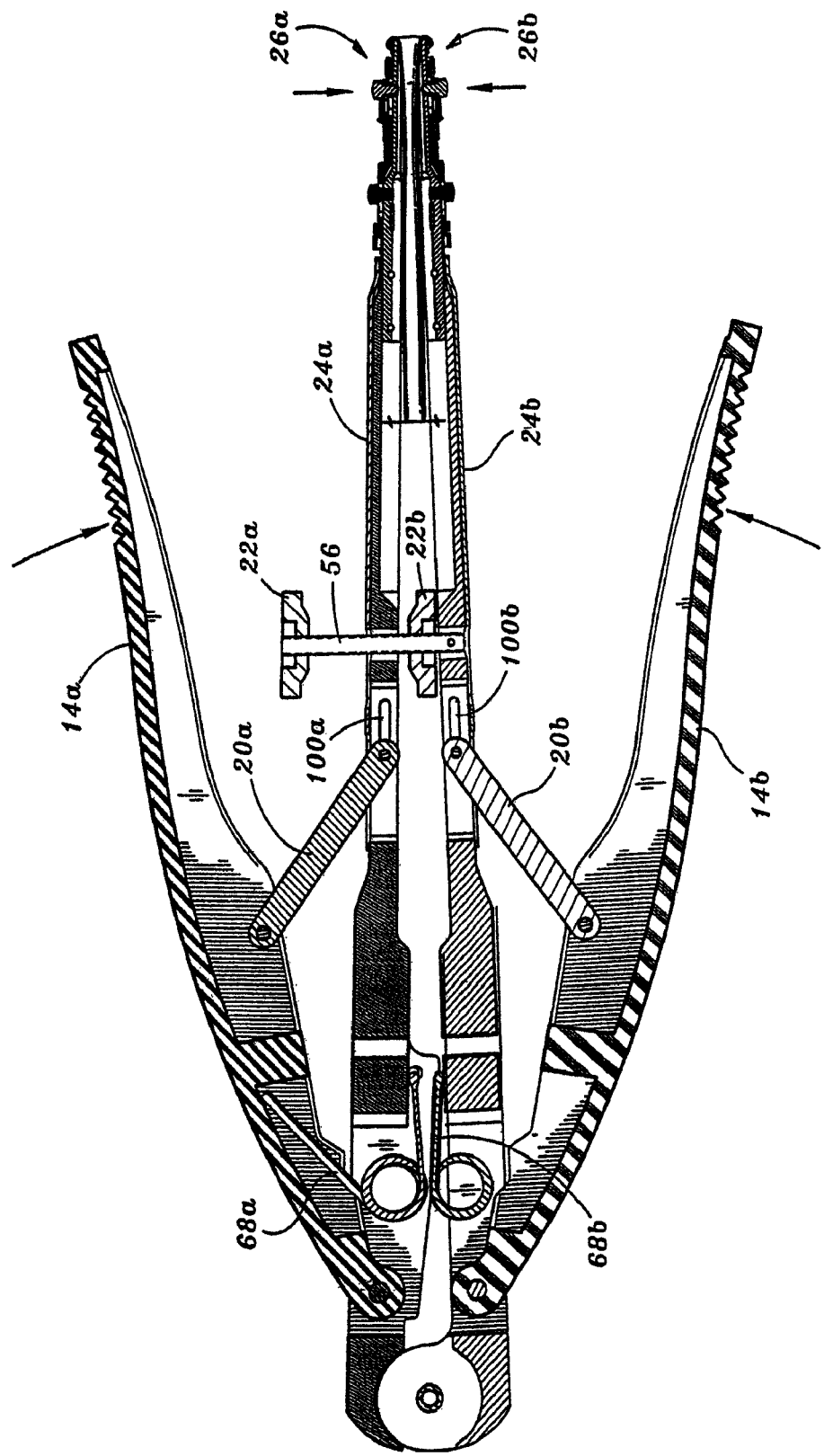
FIG. 16 is a horizontal cross-sectional view of the surgical instrument shown with upper and lower portions being biased toward each other to facilitate loading of the "heel" portion of the IMA.
Figure 17:
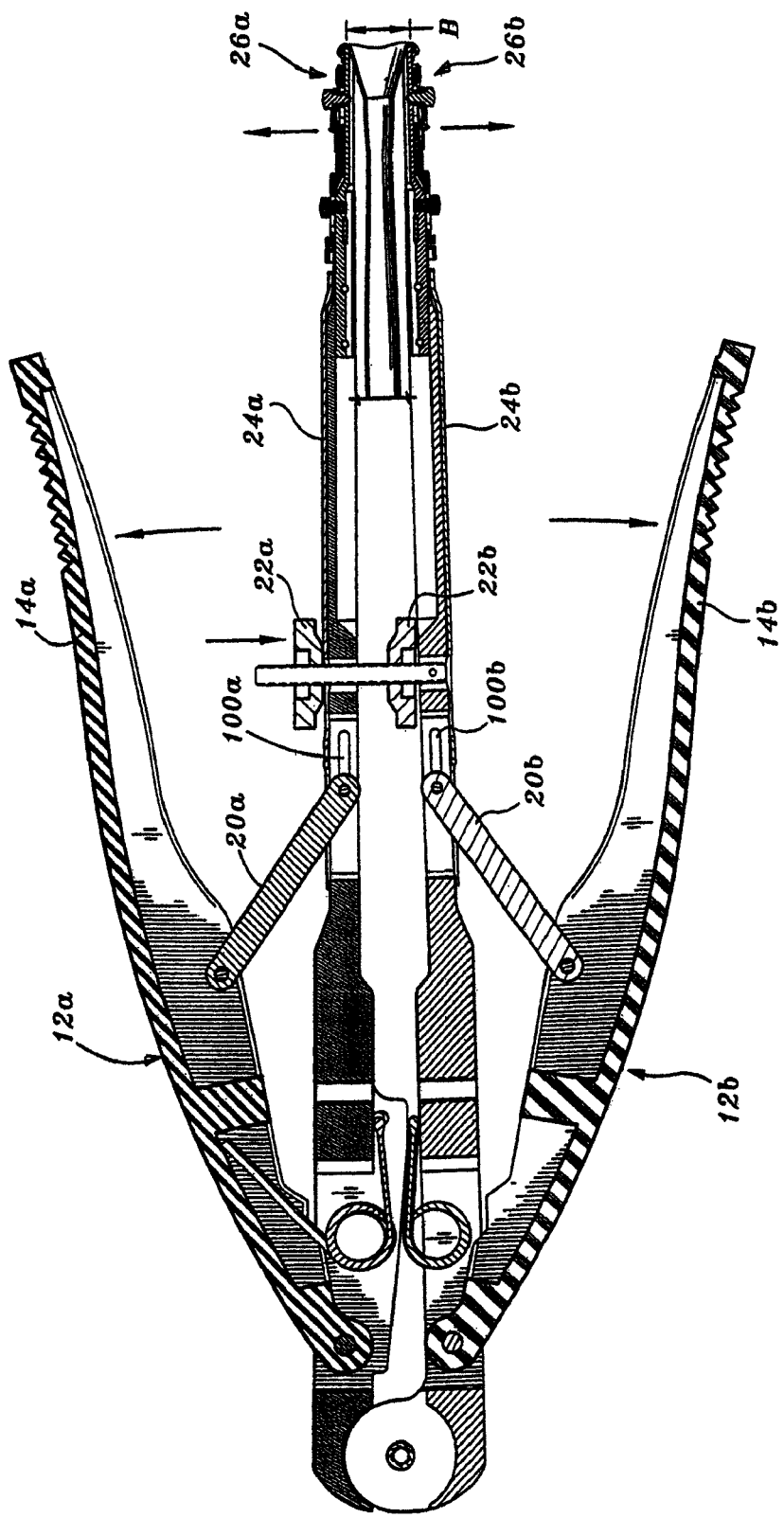
FIG. 17 is a horizontal cross-sectional view of the surgical instrument showing the upper locking dial being selectively positioned to a fixed distance between the upper and lower portions, which enables the user to approximate the size of the distal opening of the IMA.

FIGS. 16 and 17 show the two-step process for approximating the size of the distal opening of the IMA 120 prior to insertion into the LAD 128, to prevent the IMA 120 from being overexpanded within the LAD 128. The user again squeezes the handles 14a and 14b which, in turn, pivotally move the fastener support members 26a and 26b toward one another. Tissue prongs 40a1, 40a2 and 40b1, 40b2 retain the end portion 124 of the IMA 120 atop the plurality of surgical fasteners 110. The user then gradually releases the handles 14a, 14b to establish the desired expanded position of the distal opening of the IMA 120 as illustrated by reference letter "B" and then rotates dial 22a about standoff 56 such that dial 22a abuts upper portion 12a thus restricting the vertical movement of the upper portion 12a between dials 22a and 22b as seen best in FIG. 17. After the handles 14a, 14b are released, the user can incrementally adjust the size of the opening "B", e.g., smaller or larger, by rotating the dial 22a in the proper direction to effect the same. This approximates the desired expanded size of the distal opening of the IMA 120 prior to insertion in the LAD.

Turning now to FIGS. 19-23 which show the IMA 120 being inserted through an incision 130 formed in the LAD 128. More particularly and as best shown in FIG. 20, the user again squeezes the handles 14a, 14b relative to one another which move the fastener support members 26a, 26b toward one another, as illustrated by reference letter "A". The user then inserts the distal ends of the fastener support members 26a, 26b into the incision 130 such that the distal end of each of the plurality of fasteners 110 and the everted end portions 124 of the IMA tissue 120 are sufficiently inserted into and through incision 130. As seen best in the enlarged view of FIG. 21, the proximal ends of the surgical fasteners 110 remain outside incision 130.

The user then releases the handles 14a, 14b such that the opening of the IMA 120 expands to its predetermined approximated distance "B" within the incision 130 as best seen in FIGS. 22 and 23. Once the IMA 120 is properly expanded within the LAD 128, the user then rotates dial 22b about standoff 56 towards upper portion 12a such that dial 22b abuts and biases portion 12a against portion 12b. The instrument is now preset for firing.

FIGS. 24-33 show the firing sequence of instrument 10, i.e., when the handles 14a, 14b are squeezed by the user. More particularly, FIGS. 24, 25, 27, 28, 29, 31, 32 and 33 show the firing of the upper fastener support member 26a. It is to be understood that the lower fastener support member 26b and its respective component parts is fired simultaneously with the upper fastener support member 26a.

Figure 24:
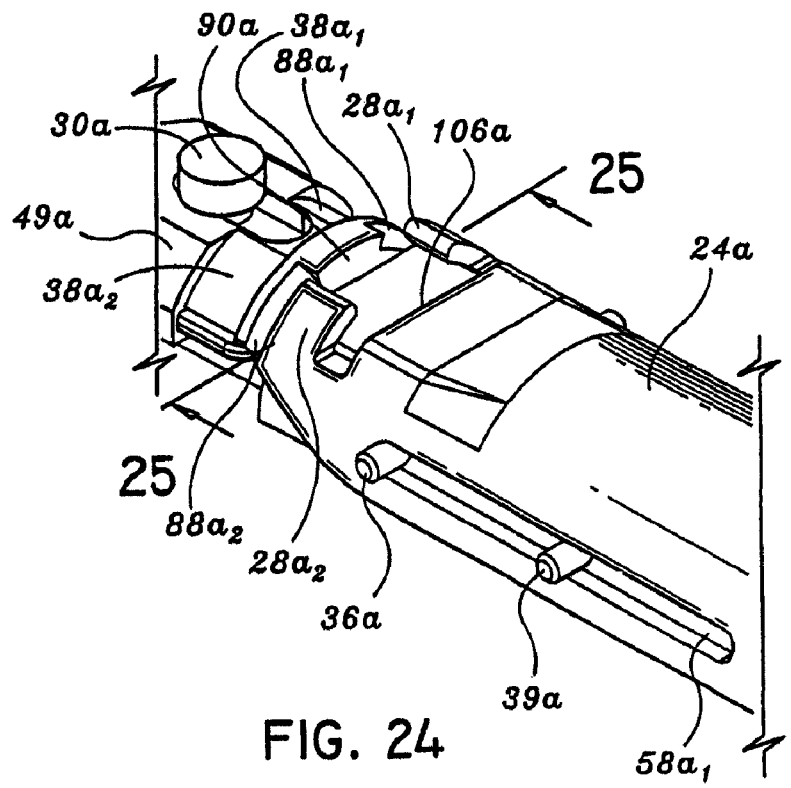
FIG. 24 is a partial perspective view of a pusher member prior to engagement with an anvil of the firing piston.
Figure 25:
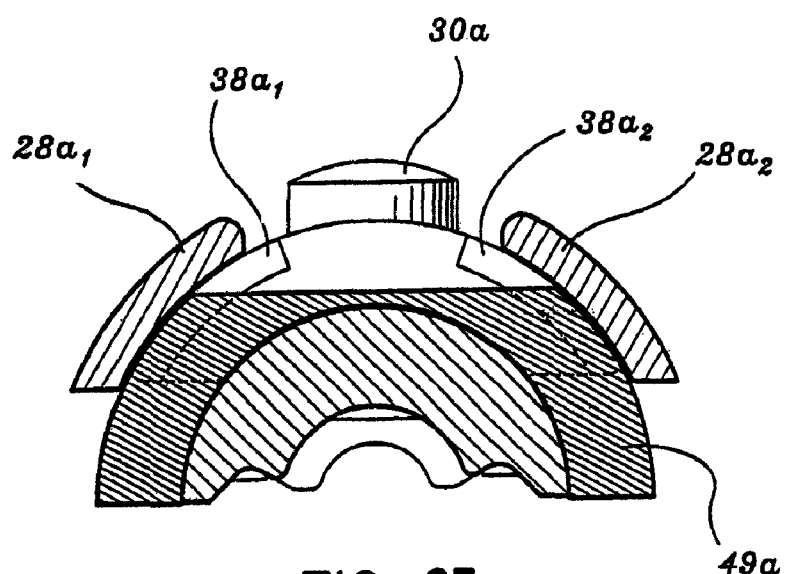
FIG. 25 is an enlarged, cross-sectional view taken along section line 25-25 of FIG. 24.

FIGS. 24 and 25 show the distal portion of the pusher member 24a prior to engagement with the firing piston 34a. Thereafter, the user squeezes the two handles 14a, 14b and since portions 12a and 12b are now locked relative to one another, movement of the handles now causes the actuating link bars 20a and 20b to slide distally within side channels 100a, 99a and 100b, 99b as shown in FIG. 26. Simultaneously, and as shown with respect the upper portion 12a, hammers 28a1 and 28a2 are urged over the cam surfaces 88a1 and 88a2 (see FIG. 28) of semi-annular rims 86a, 86b. Slide pins 36a and 39a assure consistent longitudinal movement of the pusher member 24a within slots 58a1 and 58a2.

As the user continues to squeeze the handles 14a, 14b together, the pusher hammers 28a1 and 28a2 continue to move distally to clear the cammed surfaces 88a1 and 88a2 and engage their respective hammer captures 38a1 and 38a2 as best shown in FIG. 32. As can be appreciated, this locks pusher member 24a to the firing piston 34a. Once engaged, the leading distal edge 106a of pusher member 24a abuts rear stop 90a which operates to limit further distal movement of the pusher member 24a with respect to the firing pistons 34a.

As the user continues to squeeze the handles 14a, 14b, together, the actuating link bars 20a, 20b impart longitudinal movement to the pusher members 24a, 24b against the firing pistons 34a, 34b (See FIGS. 26-29), which, in turn, drive hammers 59a1, 59a2, 59a3 (and 59b1, 59b2 and 59b3 (not shown in this figure)), distally to deform fasteners 110 and securely fasten the IMA 120 to the LAD 128 in fluid communication as shown in FIGS. 30 and 31.

Referring to FIGS. 32 and 33, upon release of the handles 14a, 14b, torsion springs 68a, 68b bias the handles outwardly thereby returning the pusher members 24a, 24b to their pre-fired position. Since the pusher members 24a, 24b and the firing pistons 34a, 34b are now engaged with one another, the firing pistons 34a, 34b together with the fastener support members 26a, 26b also retract proximally in response to the release of the handles 14a, 14b as seen best in FIG. 32. In particular, the tissue clamps 40a1, 40a2 and 40b1, 40b2 (see FIG. 18) retract upon release of the handles 14a, 14b due to the frictional engagement between the actuating sleeves 42a, 42b and the clamping clip 43a, 43b as shown best in FIG. 33.

Figure 34:
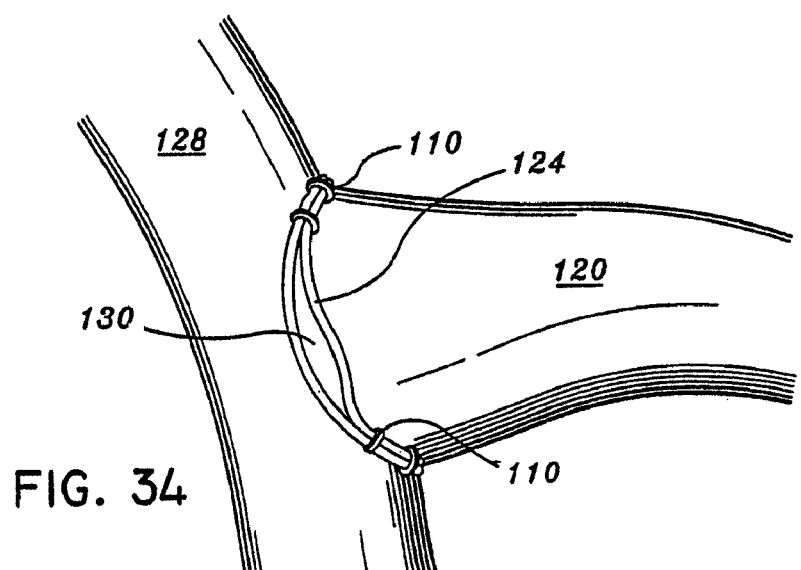
FIG. 34 is a view showing the "heel" and "toe" of the IMA attached to the LAD.
Figure 35:
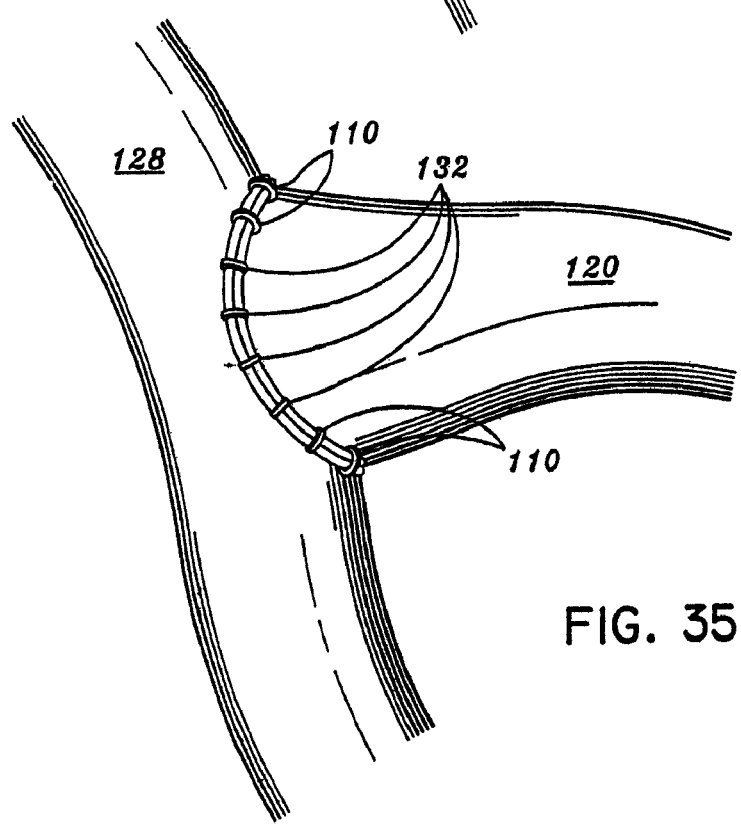
FIG. 35 is a view showing the completed anastomosis.

FIG. 34 shows the result of the firing of the surgical instrument 10, i.e., the "heel" and "toe" of the IMA 120 are attached to the LAD 128 by way of a plurality of surgical fasteners 110. As can be appreciated, once the "heel" and "toe" of the IMA 120 are secured, the user can complete the anastomosis by securing additional surgical fasteners 132 to the side portions between the two vessels 120, 128 as depicted in FIG. 35.

It will be understood that various modifications may be made to the embodiment shown herein. For example, the instruments may be sized to perform an anastomosis for other vessels and luminal tissue. Therefore, the above description should not be construed as limiting, but merely as exemplifications of preferred embodiments. Those skilled in the art will envision other modifications within the scope and spirit of the claims appended hereto.

What is claimed is:

1. A surgical instrument for performing an anastomosis, which comprises:
   a housing having a pair of opposed housing portions each having a proximal end and a distal end, the proximal ends being pivotally connected to one another and the distal ends being selectively movable toward and away from each other to define an approximation distance therebetween;
   an approximation control mechanism operatively associated with the first and second opposed housing portions to selectively move the distal ends of the opposed housing portions toward and away from each other, the approximation control mechanism including a standoff member which connects the first and second housing portions and an approximation adjusting member that engages the standoff member, wherein one of the first and second opposed housing portions is movable relative to the other of the opposed housing portions in response to movement of the adjusting member with respect to the standoff member to selectively set a maximum approximation distance;
   a fastener support member attached to the distal end of the housing configured and dimensioned to releasably retain a plurality of surgical fasteners; and
   an actuating assembly operatively associated with the fastener support member to facilitate deformation of at least a portion of the surgical fasteners.

2. A surgical instrument according to claim 1, wherein the standoff member connects the first and second housing portions.

3. A surgical instrument according to claim 1, wherein the approximation control mechanism further includes an approximation control locking member which engages the standoff member and locks the relative approximation distance between the first and second opposed housing portions.

4. A surgical instrument according to claim 1, further including a tissue retaining mechanism which is selectively operable to retain tissue adjacent the surgical fasteners prior to deformation.

5. A surgical instrument according to claim 1, wherein the fastener support member includes a first fastener support member extending distally from a first of the opposed housing portions and a second fastener support member extending distally from a second of the opposed housing portions, wherein the first fastener support member includes a first hammer portion and a first firing piston and the second fastener support member includes a second hammer portion and a second firing piston.

6. A surgical instrument according to claim 5, further including a fastener firing mechanism associated with the first and second fastener support members, the fastener firing mechanism including a pusher mechanism, wherein the pusher mechanism is movable to simultaneously deform the plurality of surgical fasteners.

* * * * *

UNITED STATES PATENT AND TRADEMARK OFFICE
CERTIFICATE OF CORRECTION

PATENT NO. : 8,123,102 B2  Page 1 of 1
APPLICATION NO. : 13/227981
DATED : February 28, 2012
INVENTOR(S) : Scott E. Manzo It is certified that error appears in the above-identified patent and that said Letters Patent is hereby corrected as shown below:

On the title page:

Under "Related U.S. Application Data" please add:

The Application Serial No. 10/182,215 is a 35 U.S.C. § 371 National Filing of PCT/US01/02043 filed January 18, 2001.

Signed and Sealed this
Twenty-fourth Day of April, 2012

David J. Kappos
*Director of the United States Patent and Trademark Office*